(12) United States Patent
Lakshmi et al.

(10) Patent No.: US 7,959,954 B2
(45) Date of Patent: Jun. 14, 2011

(54) PHARMACEUTICAL COMPOSITION FOR TREATMENT OF DIABETES AND DYSLIPIDEMIA

(75) Inventors: Vijai Lakshmi, Lucknow (IN); Ajet Saxena, Lucknow (IN); Rajesh Kumar, Lucknow (IN); Raghwendra Pal, Lucknow (IN); Satyawan Singh, Lucknow (IN); Arvind Kumar Srivastava, Lucknow (IN); Preeti Tiwari, Lucknow (IN); Deepak Raina, Lucknow (IN); Anil Kumar Rastogi, Lucknow (IN); Mahendra Nath Srivastava, Lucknow (IN); Ramesh Chandra, Lucknow (IN); Anju Puri, Lucknow (IN); Ram Raghubir, Lucknow (IN); Poonam Gupta, Lucknow (IN); Narender Tadigoppula, Lucknow (IN); Brijendra Kumar Tripathi, Lucknow (IN); Sudhir Srivastava, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/519,327

(22) Filed: Sep. 11, 2006

(65) Prior Publication Data
US 2007/0178179 A1 Aug. 2, 2007

(30) Foreign Application Priority Data
Sep. 12, 2005 (IN) .......................... 2464/DEL/2005

(51) Int. Cl.
*A61K 36/00* (2006.01)
*A61K 38/00* (2006.01)
(52) U.S. Cl. ............ 424/725; 424/769; 514/7.4; 514/6.8
(58) Field of Classification Search ........................ None
See application file for complete search history.

(56) References Cited

U.S. PATENT DOCUMENTS
4,675,188 A * 6/1987 Chu
2001/0055627 A1 * 12/2001 Guthrie et al. ................ 424/736
2002/0198796 A1 12/2002 White et al.

FOREIGN PATENT DOCUMENTS
CN 1513853 A * 7/2004
JP 2000072684 A * 3/2000
WO WO 02/077761 A2 10/2002

OTHER PUBLICATIONS

Uddin et al, Antidiarrhoeal activity of the methanol extract of the barks of *Xylocarpus moluccensis* in castor oil-and magnesium sulphate-induced diarrhea models in mice, Journal of Ethnopharmacology 101 (2005) 139-143.*
Saxena et al, Constituents of *Carapa granatum* fruits, Fitoterapia 72 (2001) 186-187.*
Mulholland et al, Limonoids from Australian members of the meliaceae, Phytochemistry, 31 (12): 4163-4166, 1992), and further in view of Chu (US 4,675,188.*
Kudo et al, The structure of xylomollin, a secoiridoid hemiacetal acetal, Journal of the American Chemical Society 98 (21) 6704-6705, 1976.*
Xiao et al, Xyloccensin K extracted from *Xylocarpus granatum* (muguodong) studied by NMR spectroscopy, Bopuxue Zazhi (2005), 22 (3), 315-319.*
Alvi, Limonoids from the Fijian medicinal plant dabi (*Xylocarpus*), Tdtrahedron 47 (43): 8943-8948, 1991.*

* cited by examiner

*Primary Examiner* — Qiuwen Mi
(74) *Attorney, Agent, or Firm* — Winston & Strawn LLP

(57) ABSTRACT

A bioactive fraction obtained from *Xylocarpus* that is useful for the treatment of diabetes and dyslipidemia. This fraction can be provided in a pharmaceutical composition that is useful as antidiabetic and antidyslipidemic agent, or can be used in a method of treating diabetes and dyslipidemia in a subject. Also, a process for the preparation of bioactive fraction from *Xylocarpus*. Isomeric xyloccensins and the preparation of such compounds. Also, pharmaceutical compositions comprising a therapeutically effective amount of such isomeric xyloccensins optionally along with one or more pharmaceutically acceptable carriers, additives, lubricant and diluents and the use of such pharmaceutical compositions in a method for treating dyslipidemia.

13 Claims, 14 Drawing Sheets

Carapolide-A

Carapolide- B

Xyloccensin -H

Xyloccensin -F

ß- Sitosterol-ß- D-glucoside

Photogedunin

ß- Sitosterol palmitic acid

Figure 1:
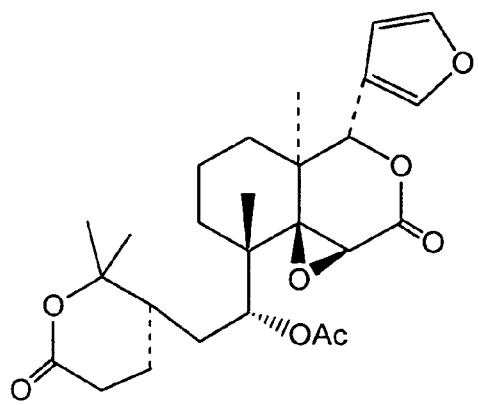

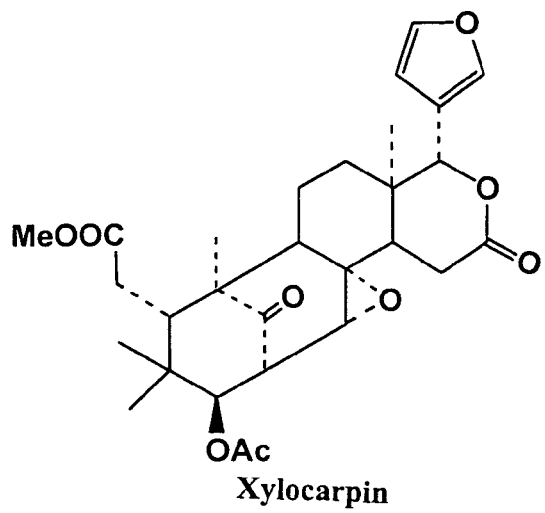
Xylocarpin
Fig 9
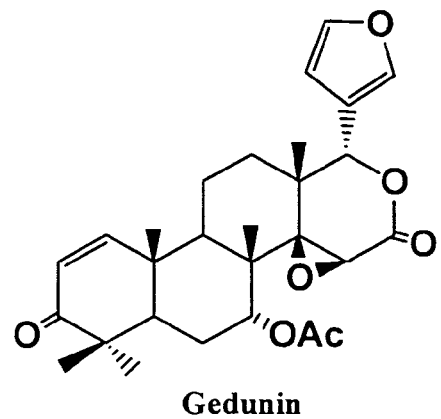
Gedunin
Fig 10
Novel isomeric xyloccensins
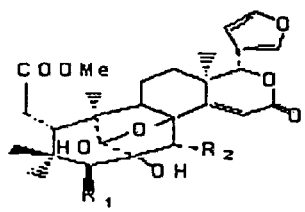
Fig 11
where
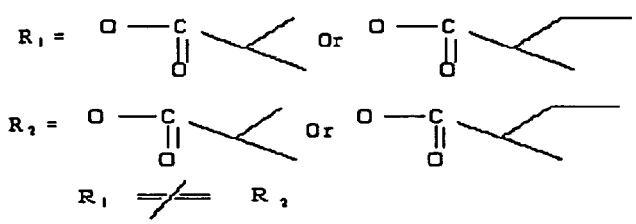

Xyloccensin X

Xyloccensin Y

Xyloccensin-E ; R-1=R-2=R-3 = OAc

Xyloccensin-E-derivative ; R-1= H, R-2=R-3= OAc

Xyloccensin-I  R-4 = O–C(=O)–CH₂–CH(CH₃)  R-5= -OH, R-6 =- OAc

Xyloccensin-J  R-4 = O–C(=O)–CH(CH₃)₂ , R-5 = OH, R-6= OAc

Xyloccensin-P  ;   R-10 = OAc, R-11 = OAc

Xyloccensin-Q  ;   R-10 = R-11 = OH

Xyloccensin-R  ;   R-10 = OAc, R-11 = OH

Xyloccensin-S  ;   R-10 = OH. R-11 = OAc

Xyloccensin-T  ;   R-10 = H, R-11 = OAc

Xyloccensin-U

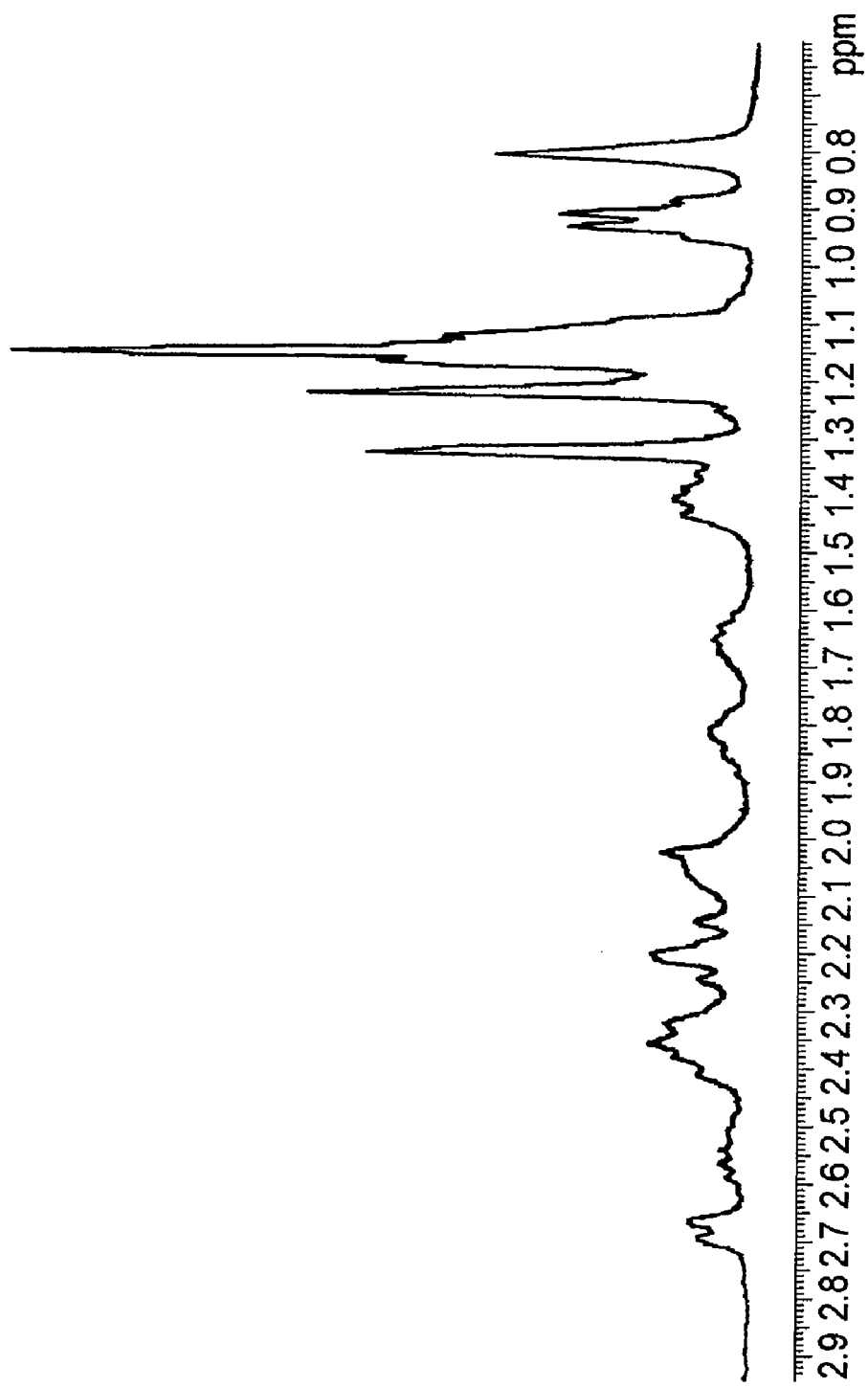

PHARMACEUTICAL COMPOSITION FOR TREATMENT OF DIABETES AND DYSLIPIDEMIA

FIELD OF INVENTION

The present invention relates to the bioactive fraction obtained from *Xylocarpus* useful for the treatment of diabetes and dyslipidemia. Further, it relates to a pharmaceutical composition useful as antidiabetic and antidyslipidemic agent. More particularly, it relates to a method of treating diabetes and dyslipidemia in a subject.

The present invention also relates to the isomeric xyloccensins and use thereof. More particularly it relates to the pharmaceutical composition comprising a therapeutically effective amount of isomeric xyloccensins optionally along with one or more pharmaceutically acceptable carriers, additives, lubricant and diluents. Further, it relates to the method of treating dyslipidemia using such pharmaceutical composition. Still further, the present invention also relates to a process for the preparation of the bioactive fractions from *Xylocarpus*.

BACKGROUND AND PRIOR ART

*Xylocarpus granatum* Koen belongs to Natural Order Meliaceae. It is a mangrove and is commonly known as "pussur" in Hindi language. It is tall tree ranging up to 20 m. with buttressed stem base. Bark is yellowish-white, peeling off as papery flakes. Leaves unijugate or bijugate, leaflets obovate, glabrous, entire, rounded at apex, tappering at base; flowers 5-7 mm. across, white with a reddish gland within, in axillary thyrses: Calyx 4-lobed, petals 4, free. Fruits are large as long as 30-40 cm. across, globose, septa fragal capsules; splitting tardily into 4 valves. Seeds 10-15 in number pyramid shaped corky testa. flowering and fruiting through out year. The species occurs in tidal forests along the east and west coastal areas up to Maharastra and in Andaman Island in India.

Seed paste is used for relief of breast cancer [Banerjee, L. K., Sastry, A. R. K. and Nayar, M. P. (1989) B.S.I. Publication; (1989), 58-59.; Chopra, R. N., Nayar, S. L. and Chopra, I. C. *Glossory of Indian Med. Plants*. (1956), 51, CSIR Publication, New Delhi, India]. Literature review revealed that only few workers have tried to isolate chemical constituent of this species. Fatty acids, sterols and hydrocarbons were isolated from its leaves [Hogg. W. R. and Gillan, T. F., *Phytochemistry* 23 (1984) 93-97]. An alkaloid 8-acetyl dihydrochelerythrins from its root bark [Krajniak, E. R., Ritchie, E. and Taylor, W. C. *Aust. J. Chem*. 26 (1973) 687].7-α-Acetoxydihydronomillin (Cneorin-G) was isolated from this plant [Marcelle, G. B. and Mootoo, B. S. *Tet. Lett*. (1981) 505; Ahmed F. R., Ang. S. Ng and Fallis, A. G., *an. J. Chem*. 56 (1978) 1020]. Xylocarpin was isolated from the seed of the plant [Okorie, D. A. and Taylor D. A. H. *J. Chem. Soc*. (C) (1970) 211]. In another report Xyloccensin—I & J were also isolated from this species [Alvi K. A., Crew, P., Aalsbersberg, B and Prasad, R., *Tetrahedron.*, 47 (1991) 8943]. Further in another report, Xyloccensin-K, a new limonoid was also isolated from the seeds [Kokpol, U. Warmthorn. C., *Phytochemist,* 41(3) (1996) 903-5], 6-α, 1-β-diacetoxygedunin were isolated from its fruits.[Saxena, E. and Babu, U. V. *Fitoterapia*, 72(2) (2001) 186-87] Xyloccensins-L,M,N,O,P,Q,R,S, T&U were isolated recently by Chineese workers [Jun Wu, Si Zhang, Qiang Xiang, Qingxin Li, Jianshe Huang, Lijuan Long and Liangmin Huang, *Tet Lett.*, 45 (2004) 591-593; Jun Wu, Si Zhang, Qiang Xiao, Qingxin Li, Jianshe Huang, Zhi- hui Xiao and Lijuan Long, Z Naturforsch, 58b, 1216-19(Abstract) full paper in press (2004), Jun Wu, Xiang Q, Jianshe Huang, Zhihui Xiao, Shuhua, Qi, Oingxin Li & Si Zhang, *Org. Lett*. 6 (11), 1841-1844 (2004), Jianxin Cui, Zhiwei Deng, Jun Li, Hongzheng Fu, Peter Proksch & Wenhan Lin, *Phytochemistry*, 66 (19), 2334-2339, (2005)]. Wu J., Xiao Q., Zhang S., Li X., Xiao Z. H., Ding H. X., Li Q. X., *Tetrahedron,* 61,8382 (2005), Jun Wu, Zhihui Xiao, Yang Song, Si Zhang, qiang Xiao, Cha Ma, Haixin Ding and Gingxin Li, *Mag. Res. Chem.*, 44, 87-89 (2006)]. All these research papers are of academic interest and no reports are available on bioactivities of isolated compounds. In one of the report Gedunin has been reported] as antidiabetic compound [Gonzalez H., Sierra M. *Proc. Natl. Symp*. (1989) and the plant to have antifilarial activity against adults worms and microfilariae of *B. pahangi* [Wan. O. A., Hashim, Y. O. Sulaim, M. Z. and Ibrahim J., *J Tropical Forest Prod*. (1996)].

*X. moluccensis* (Lamk) M. Roem. synonymous to *Carapa moluccensis* (Lamk) belongs to Natural Order Meliaceae. It is a mangrove and is commonly known as pussur and Pitakura in Hindi language. It is a tall tree ranging up to 10-12 m. tall and trunk of 60 cm diameter at the base, slightly buttressed stem. Bark is red with thick flacks. Wood red in color, leaflets7-12× 3-6 cm. ovate, acute at apex, oblique at the base, flowers 2-3 cm. across, white with red glands inside, staminal teeth obscure, anthers exceeding the teeth, stigma cup shaped, fruits 10-15 cm. across globose. This species of *Xylocarpus* is uncommon and grows in association with *Heritiera litteralis*. Flowering and fruiting from June to September. It is mainly reported 0to be found in Mahanadi deltaic region and in Andamans [Adelbert, A. G. L (1948) Bluma, 6(1) 314; Hiem, W. P. (1875) in *J. D. Hooker*, fl. Brit. India, 1, 561; Parkinson, C. E. (1923) For. Fl. Andaman Islands, p-118; Watson, J G (1928) Mal. For. Rec. 6].

Literature review revealed that some research work has been carried out on this plant to isolate the chemical constituents. Few limonoids such as Xyloccensins-A, B, C, D, E and F were isolated and characterized from the seed and timber of the plant [Conolly, J. D., Maclellan, M. O., Domingo, A., Taylor, D. A. H., *J. Chem. Soc,* Perkin trans-1 (1976) 19, 1993-6]. Xylomollin was isolated and characterized from the unripe fruits [Kubo, I. Miura, I., Nakanishi, K., *J. Am. Chem. Soc*., (1976) 8 (21) 6704-5]. Xyloccensins G, H, and I were isolated by Taylor group from this plant and structures were also established [Taylor, D. A. H., Phytochemistry (1983) 22 (5) 1297-9. Few hydrocarbons, fatty acids and fatty alcohols were identified in the waxes of the plant [Sil, P., Thakur, S., Mazumdar, S. G., Turner, E. A., Hamilton, R. J., *J. Ind Chem. Soc*. (1983) 60 (5) 508-11. Xyloccensins I and J were further isolated by Khisal et al. [Khisal, A., Alvi, P., Crews, B. A. and Regina, P., *Tetrahedron* (1991) 47 (43) 8943-8]. Conolly and his group isolated Mexicanolide from this plant [Conolly, J. D., Crindle, R. Mc. and Overton, K. H., *Tetrahedron* (1968) 24, 1489-97]. A new unsaturated aryl ketoacid and its methyl ester was isolated from this species by Bercich et al. [Bercich, M. G., Cambie, R. C., Lal, A. R., Sidwell, D., *Aust. J. Chem*. (1998) 51 (8) 795-797]. Few more limonoids i.e. detigloyl-6-deoxyswietenine acetate, phragamalin 3,30-diacetate and phragmalin 2,3,30-triacetate were also reported from this species by African group [Mulholland D. A. and Taylor, D. A. H. (1992) 31 (12) 4163-4166].

SUMMARY OF THE INVENTION

The present invention relates to a bioactive fraction obtained from *Xylocarpus* that is useful for the treatment of diabetes and dyslipidemia. This fraction can be provided in a pharmaceutical composition that is useful as antidiabetic and antidyslipidemic agent, or can be used in a method of treating diabetes and dyslipidemia in a subject. The present invention further relates to a process for the preparation of bioactive fraction from *Xylocarpus*.

The present invention also provides isomeric xyloccensins and the preparation of such isomeric xyloccensins. Also disclosed are pharmaceutical compositions comprising a therapeutically effective amount of such isomeric xyloccensins optionally along with one or more pharmaceutically acceptable carriers, additives, lubricant and diluents and the use of such pharmaceutical compositions in a method for treating dyslipidemia.

BRIEF DESCRIPTION OF THE DRAWING FIGURES

Figure 2:
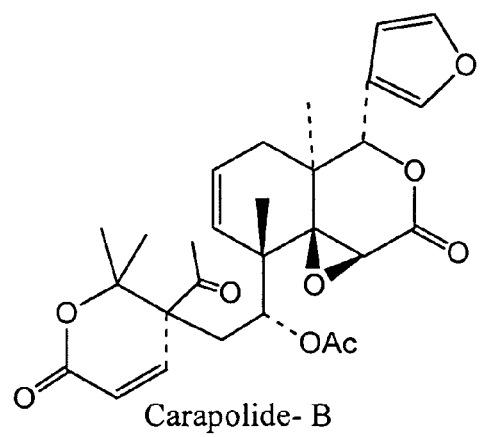
Figure 3:
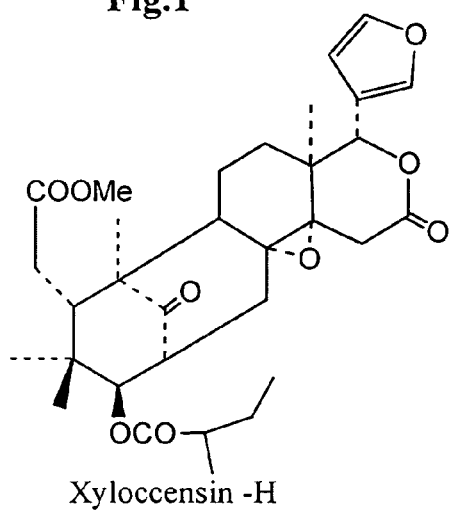
Figure 4:
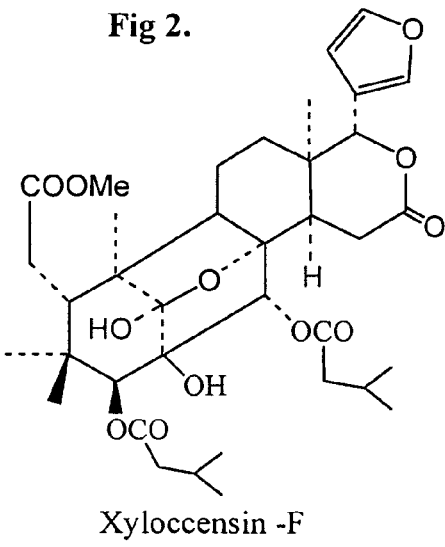
Figure 5:
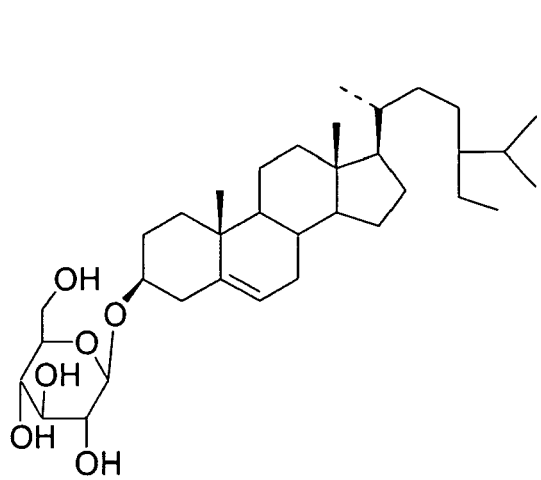
Figure 6:
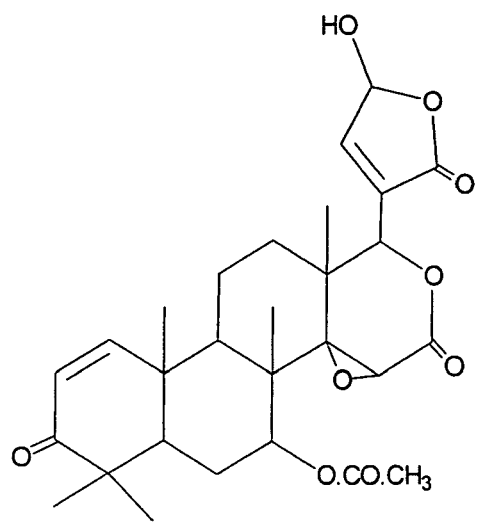
Figure 7:
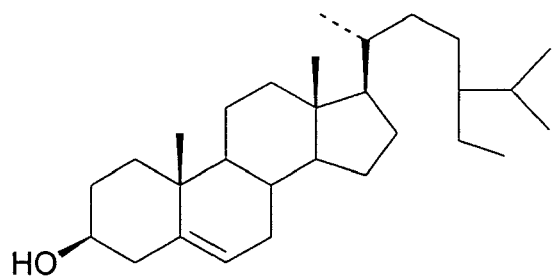
Figure 8:
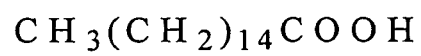
Figure 12:
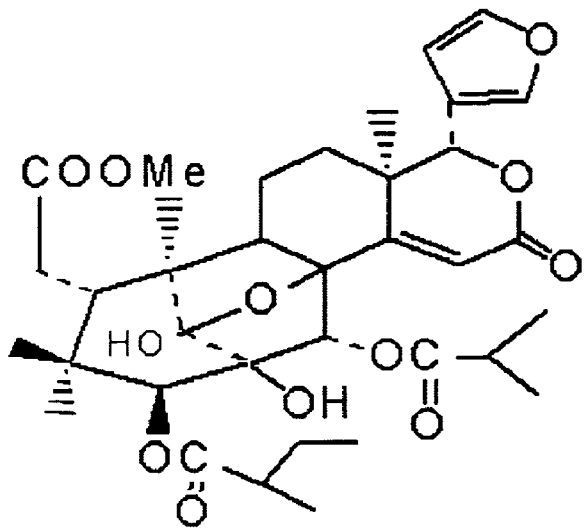
Figure 13:
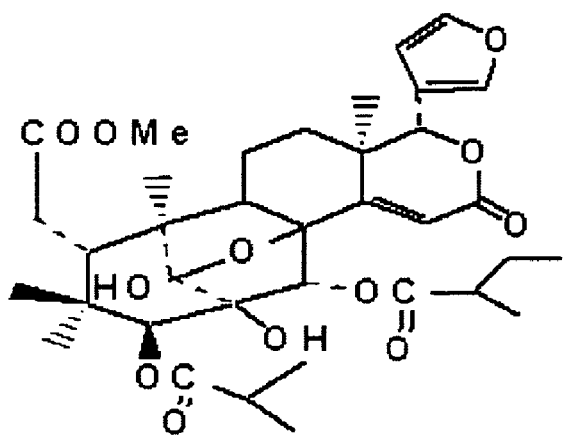
Figure 14:
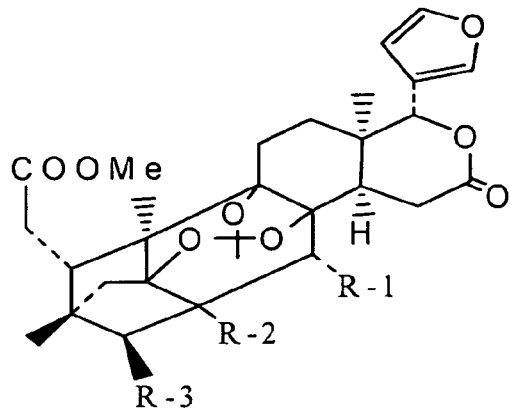
Figure 15:
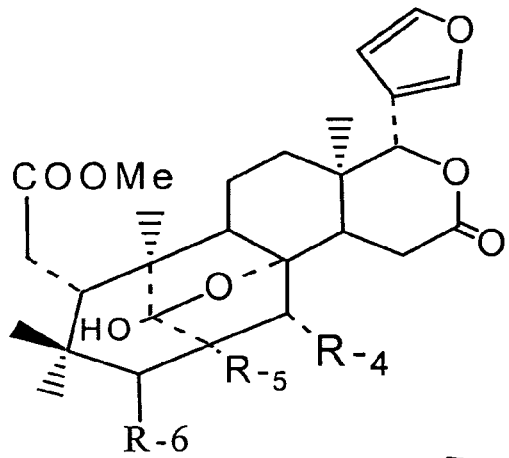
Figure 16:
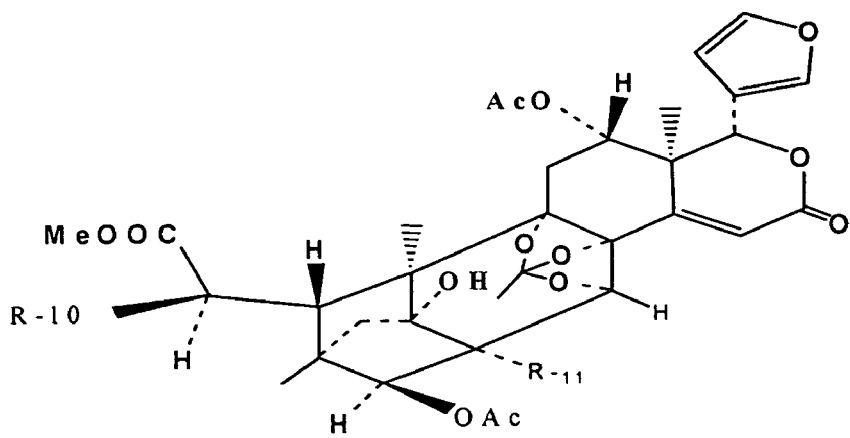
Figure 17:
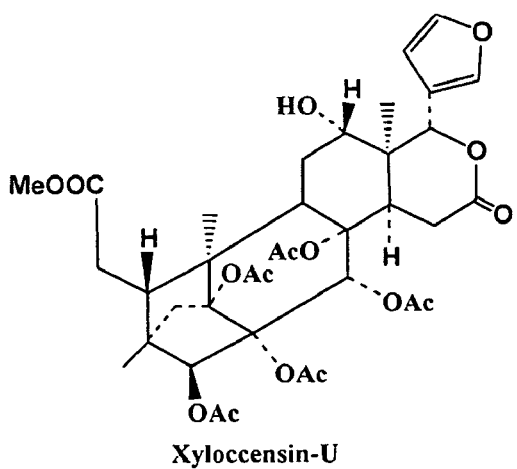
Figure 18:
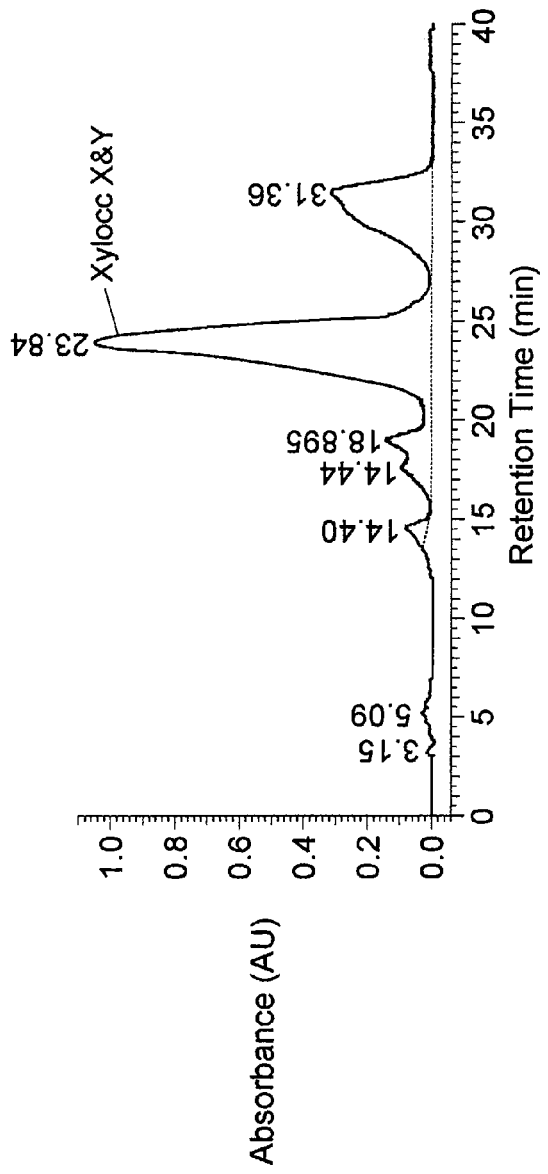
Figure 19:
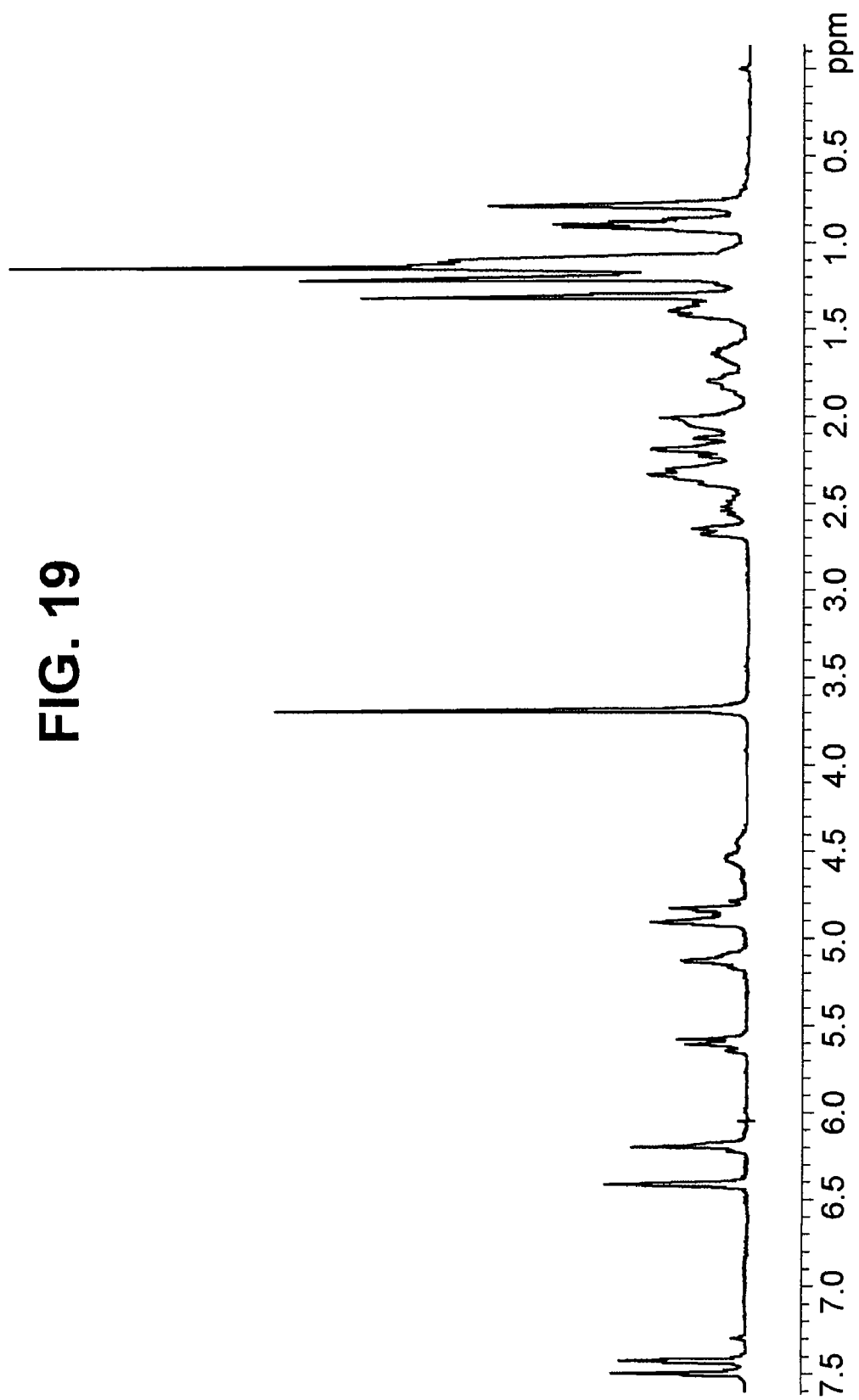
Figure 20A:
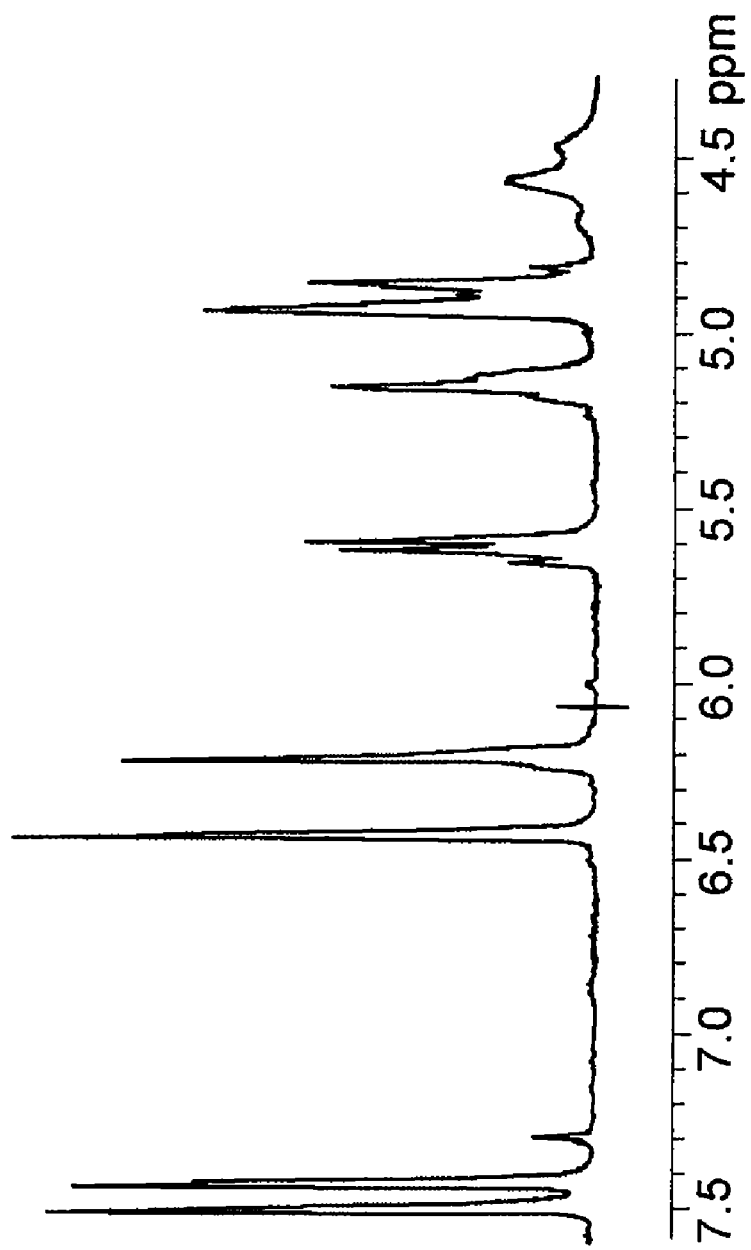
Figure 21:
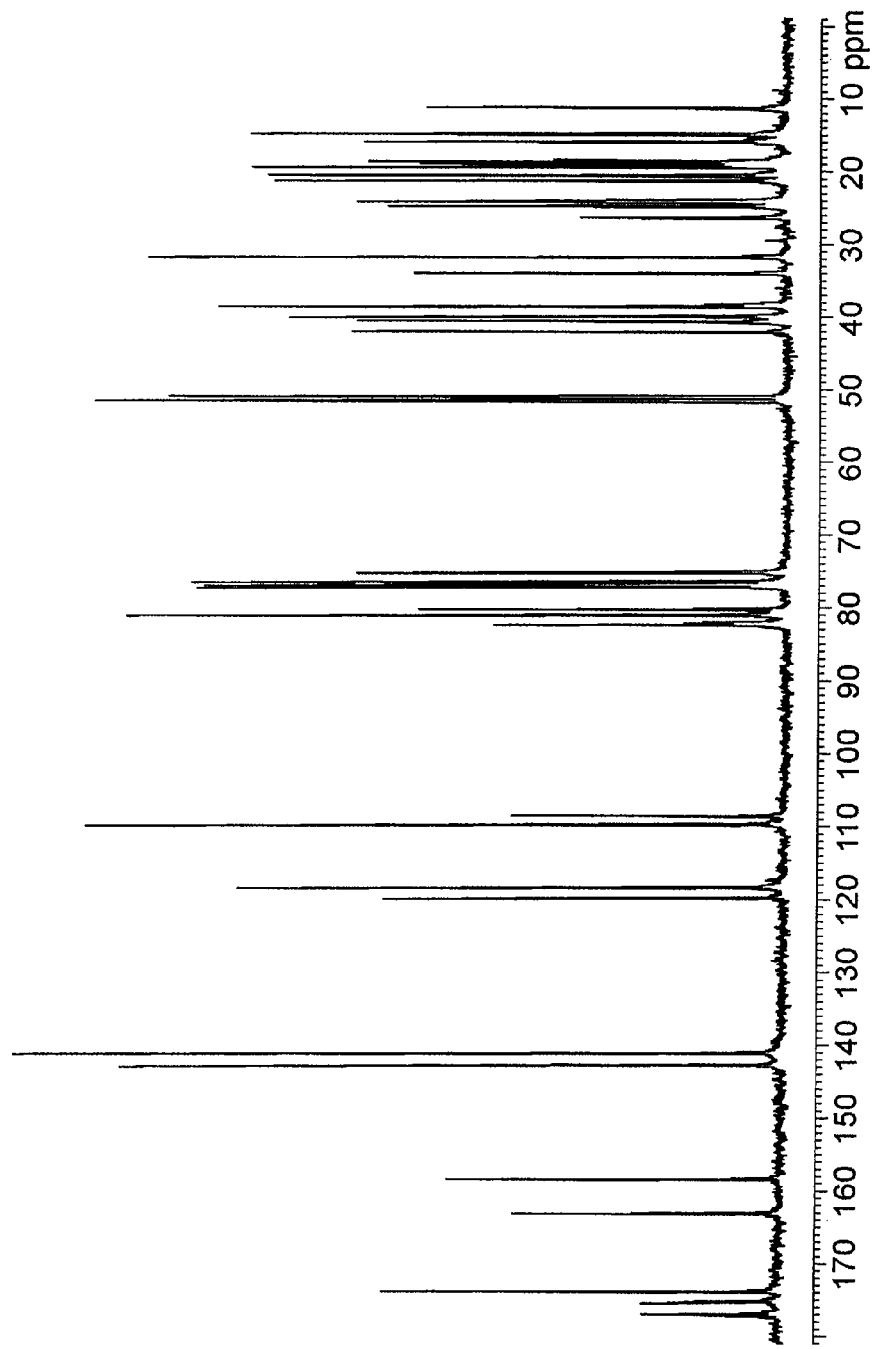
Figure 22A:
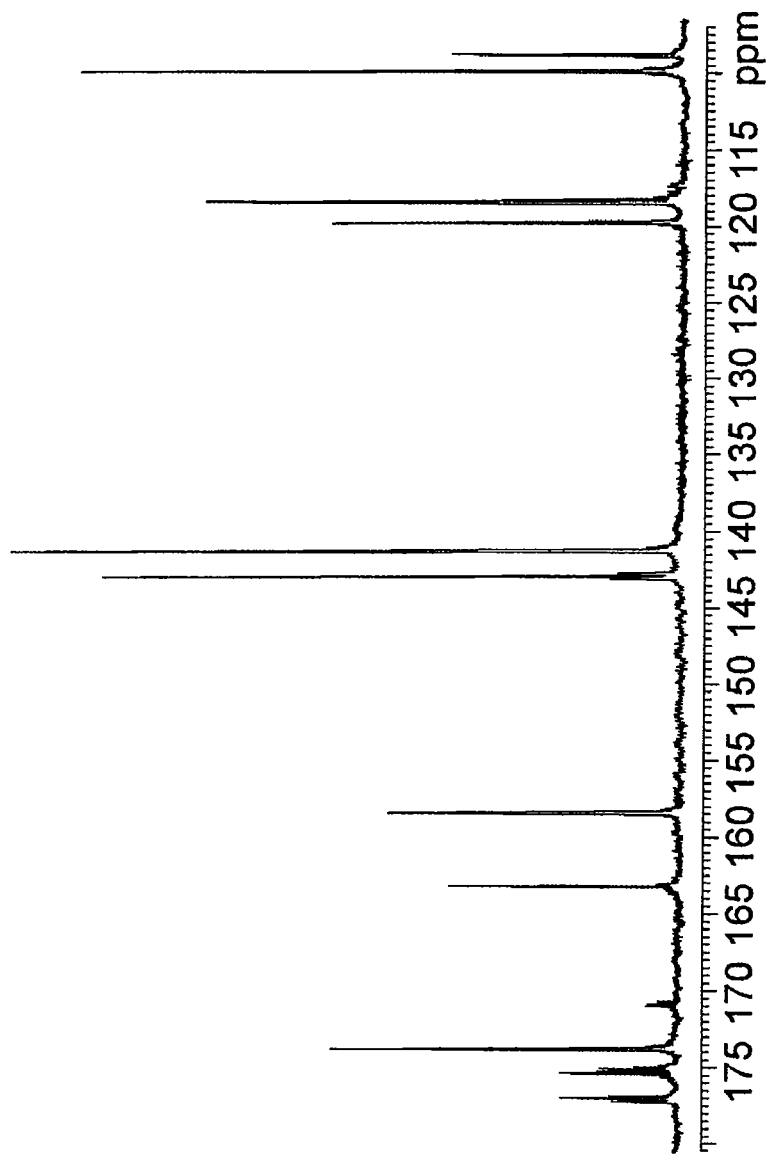
Figure 22B:
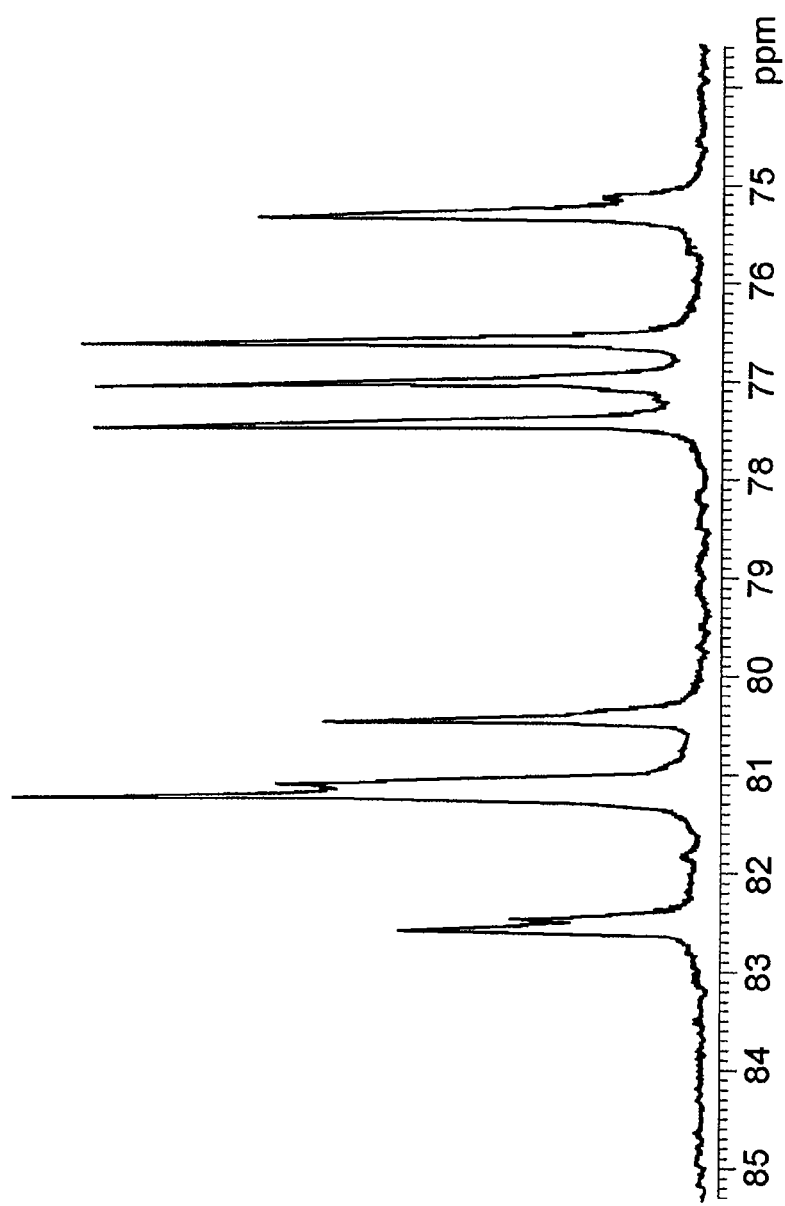
Figure 22C:
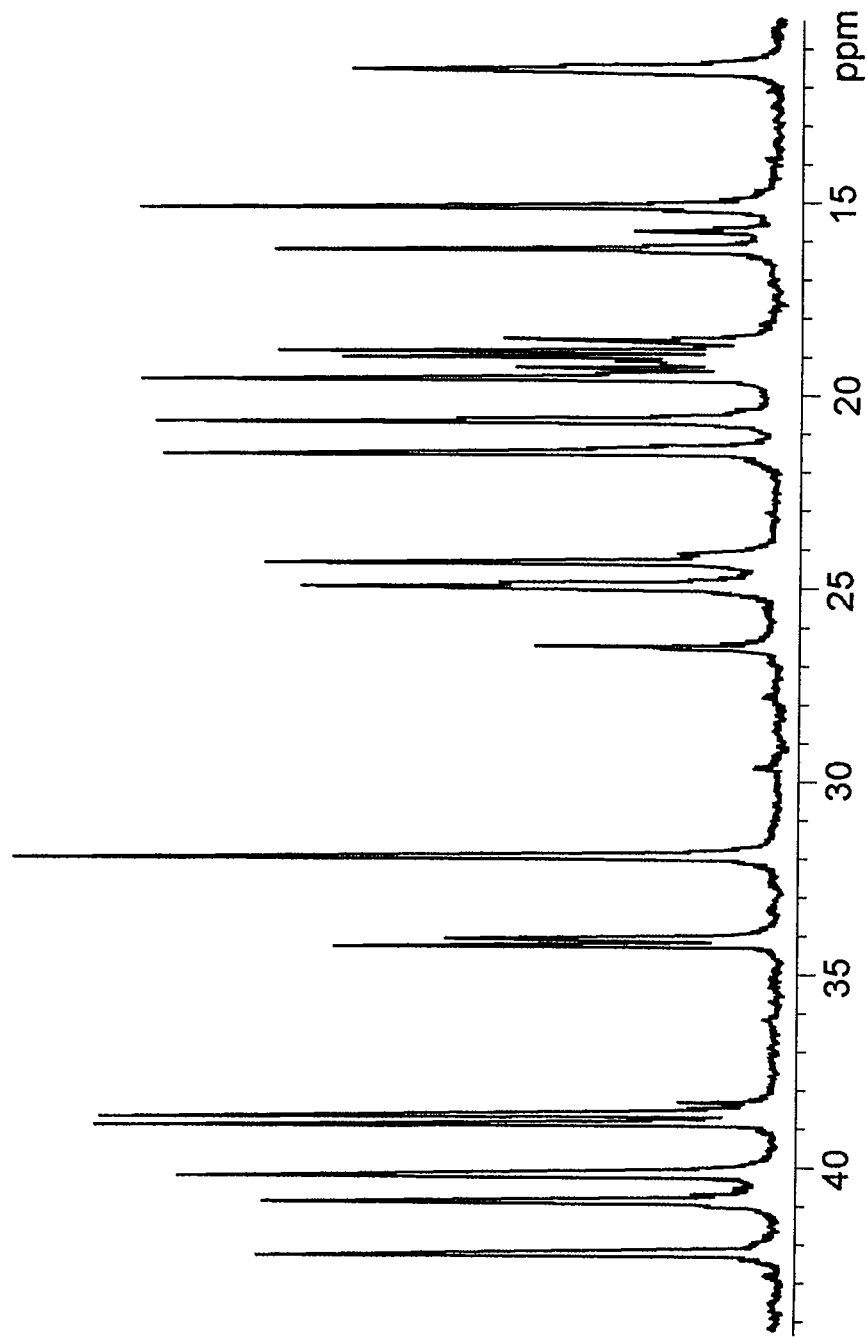

FIGS. 1-17 illustrate various compounds according to the invention, as noted below:
 FIG. 1—Carapolide—A
 FIG. 2—Carapolide—B
 FIG. 3—Xyloccensin—H
 FIG. 4—Xyloccensin—F
 FIG. 5—β—Sitosterol-β-D-glucoside
 FIG. 6—Photogedunin
 FIG. 7—β-Sitosterol
 FIG. 8—Palmitic Acid
 FIG. 9—Xylocarpin
 FIG. 10—Gedunin
 FIG. 11—isomeric xyloccensins
 FIG. 12—Xyloccensin X
 FIG. 13—Xyloccensin Y
 FIG. 14—Xyloccensin E & E derivative
 FIG. 15—Xyloccensin I & J
 FIG. 16—Xyloccensin P, Q, R, S and T
 FIG. 17—Xyloccensin U
 FIG. 18 is a HPLC chromatogram of the bioactive fraction (50% aq. EtOH extract) of *Xylocarpus Granatum* at 230 nm.
 FIG. 19 is a $H^1$ NMR spectrum of Xyloccensin X (1) and xyloccensin Y (2) in mixture.
 FIGS. 20A and 20B are illustrations of the expanded region of the $H^1$ NMR spectrum of xyloccensin X (1) and xyloccensin Y (2) in mixture.
 FIG. 21 is an illustration of a $C^{13}$ NMR Spectrum of xyloccensin X (1) and xyloccensin Y (2) in mixture.
 FIGS. 22A, 22B and 22C are illustrations of the expanded region of the $C^{13}$ NMR spectrum of xyloccensin X (1) and xyloccensin Y (2) in mixture.

DETAILED DESCRIPTION OF THE PREFERRED EMBODIMENTS

As noted, the present invention provides a bioactive fraction obtained from *Xylocarpus* useful for the treatment of diabetes and dyslipidemia. This fraction is obtained from the plant species selected from the group consisting of *Xylocarpus granatum, Xylocarpus moluccensis*. Alternatively, the fractions are obtained from any plant part of the *Xylacarpus*.

Further, the fraction may be selected from the group consisting of alcoholic fraction, chloroform fraction or chromatographic fraction. The alcoholic fraction may be either 50% alcoholic fraction (fraction a) or 95% alcoholic fraction (fraction c). The 50% alcoholic fraction (fraction a) typically comprises an ash content of about 20%-35%, an acid insoluble ash content of about 2%-3%, an ethylacetate extractive content of about 2%-5%, a n-butanol extractive content of about 5%-15%, a marker (Gedunin) content of about 1%-2.5% and an amount of an unidentified unresolved fraction.

The 50% alcoholic fraction (fraction a) may be obtained from epicarp of Xylocarpus granatum. This 50% alcoholic fraction (fraction a) shows optimum antidiabetic activity at a preferred unit dose of at least 250 mg/Kg body weight wherein the sugar level is lowered up to 28.7% with the weight percentages representing percentages of the total weight of the sugar. Also, the 50% alcoholic fraction (fraction a) shows optimum antidyslipidemic activity at a preferred unit dose of at least 500 mg/Kg body weight wherein the total glyceride level is lowered up to 60% with the weight percentages representing percentages of the total weight of the glycerides.

The 95% alcoholic fraction (fraction c) may be obtained from whole fruit of *Xylocarpus moluccensis*. This 95% alcoholic fraction (fraction c) shows optimum antidiabetic activity at a preferred unit dose of at least 250 mg/Kg body weight wherein the sugar level is lowered up to 25.5% with the weight percentages representing percentages of the total weight of the sugar. The 95% alcoholic extract (fraction c) shows optimum antidyslipidemic activity at a preferred unit dose of at least 500 mg/Kg body weight wherein the total glyceride level is lowered up to 79% with the weight percentages representing percentages of the total weight of the glycerides.

The chloroform fractions (fractions b and d) may be obtained from either 50% alcoholic fraction (fraction a) or 95% alcoholic fraction (fraction c). The chloroform fraction (fraction b) can also be obtained from 50% alcoholic fraction (fraction a). The chloroform fraction (fraction b) comprises Gedunin (14 to 19.8%), Photogedunin (1 to 1.5%) Carapolide-A (0.5 to 0.959%), Carapolide-B (0.01 to 0.279%), Xylocarpin (0.001 to 0.1%), Xyloccensin-H (0.01 to 1.7%), Xyloccensin-I (10 to 14.22%), Xyloccensin-U&F (3.5 to 6.7%), Palmitic acid (1.2 to 1.5%) β-Sitosterol-β-D-glucoside (0.9 to 1%), β-Sitosterol (2 to 2.1%), Oxogedunin (0.001 to 0.0001%), along with xyloccensin-T (3.5 to 5.8%) Xyloccensin-P 758 (4 to 7.067%), 674 xyloccensin-Q (10 to 13.65%), xyloccensin—R & xyloccensin-S (2 to 2.1%) and an unidentified unresolved fraction.

The chloroform fraction (fraction b) shows optimum antidiabetic activity at a preferred unit dose of at least 100 mg/Kg body weight wherein the sugar level is lowered up to 22.3% with the weight percentages representing percentages of the total weight of the sugar. The chloroform fraction (fraction b) shows optimum antidyslipidemic activity at a preferred unit dose of at least 125 mg/Kg body weight wherein the total glycerides level is lowered up to 63% with the weight percentages representing percentages of the total weight of the total glycerides.

The chloroform fraction (fraction d) may be obtained from 95% alcoholic fraction (fraction c). This chloroform fraction (fraction d) comprises xyloccensin E (0.2-0.32%), xyloccensin I (0.22-0.32%), xyloccensin J (0.5-0.6%), xyloccensins X&Y (0.8-1%), phragmalin diacetate (5 to 8% of the chloroform fraction), palmitic acid (1 to 1.2% of the chloroform fraction), β-sitosterol (1.5 to 1.8% of the chloroform fraction) β-sitosterol-β-D-glucoside (0.1 to 0.15% of the chloroform fraction), protolimonoids (0.01 to 0.015% of the chloroform fraction), unidentified compounds (1.1-1.2%) and a unidentified unresolved fraction. The gedunin is not present in the chloroform fraction (fraction d) The chloroform fraction (fraction d) shows optimum antidiabetic activity at a preferred unit dose of at least 100 mg/Kg body weight wherein the sugar level is lowered up to 10.1% with the weight percentages representing percentages of the total weight of the sugar. The chloroform fraction (fraction d) also shows optimum antidyslipidemic activity at a preferred unit dose of at least 250 mg/Kg body weight wherein the total glyceride level is lowered up to 89% with the weight percentages representing percentages of the total weight of the glycerides.

The chromatographic fraction (fraction e) may be obtained from the chloroform fraction (fraction d). The chromatographic fraction (fraction e) comprises mixture of limonoids. The chromatographic fraction (fraction e) shows optimum antidiabetic activity at a preferred unit dose of at least 25 mg/Kg body weight wherein the sugar level is lowered up to 52.1% with the weight percentages representing percentages of the total weight of the sugar. The chromatographic fraction (fraction e) shows optimum antidyslipidemic activity at a preferred unit dose of at least 100 mg/Kg body weight wherein the total glycerides level is lowered up to 75% with the weight percentages representing percentages of the total weight of the total glycerides.

The present invention also provides the use of the bioactive fraction obtained from $Xylocarpus$ in the treatment of diabetes and dyslipidemia. The 50% alcoholic fraction (fraction a) shows optimum antidiabetic activity at a preferred unit dose of at least 250 mg/Kg body weight wherein the sugar level is lowered up to 28.7% with the weight percentages representing percentages of the total weight of the sugar. The 50% alcoholic fraction (fraction a) also shows optimum antidyslipidemic activity at a preferred unit dose of at least 500 mg/Kg body weight wherein the total glycerides level is lowered up to 60% with the weight percentages representing percentages of the total weight of the total glycerides.

The 95% alcoholic fraction (fraction c) shows optimum antidiabetic activity at a preferred unit dose of at least 250 mg/Kg body weight wherein the sugar level is lowered up to 25.5% with the weight percentages representing percentages of the total weight of the sugar. The 95% alcoholic extract (fraction c) also shows optimum antidyslipidemic activity at a preferred unit dose of at least 500 mg/Kg body weight wherein the total glycerides level is lowered up to 79% with the weight percentages representing percentages of the total weight of the total glycerides.

The chloroform fraction (fraction b) shows optimum antidiabetic activity at a preferred unit dose of at least 100 mg/Kg body weight wherein the sugar level is lowered up to 22.3% with the weight percentages representing percentages of the total weight of the sugar. The chloroform fraction (fraction b) shows optimum antidyslipidemic activity at a preferred unit dose of at least 125 mg/Kg body weight wherein the total glycerides level is lowered up to 63% with the weight percentages representing percentages of the total weight of the total glycerides.

The chloroform fraction (fraction d) shows optimum antidiabetic activity at a preferred unit dose of at least 100 mg/Kg body weight wherein the sugar level is lowered up to 10.1% with the weight percentages representing percentages of the total weight of the sugar. The chloroform fraction (fraction d) also shows optimum antidyslipidemic activity at a preferred unit dose of at least 250 mg/Kg body weight wherein the total glycerides level is lowered up to 89% with the weight percentages representing percentages of the total weight of the total glycerides.

The chromatographic fraction (fraction e) shows optimum antidiabetic activity at a preferred unit dose of at least 25 mg/Kg body weight wherein the sugar level is lowered up to 52.1% with the weight percentages representing percentages of the total weight of the sugar. The chromatographic fraction (fraction e) also shows optimum antidyslipidemic activity at a preferred unit dose of at least 100 mg/Kg body weight wherein the total glycerides level is lowered up to 75% with the weight percentages representing percentages of the total weight of the total glycerides.

The present invention also provides the use of the bioactive fraction obtained from $Xylocarpus$ in the treatment of diabetes and dyslipidemia. Further, the present invention provides a pharmaceutical composition useful as antidiabetic and antidyslipidemic agent comprising a therapeutically effective amount of bioactive fractions optionally along with one or more pharmaceutically acceptable carriers, additives and diluents. These diluents may be selected from the group consisting of starch, lactose, dicalcium phosphate. A lubricant selected from the group consisting of talc, magnesium stearate amy also be used.

The composition may comprise a therapeutically effective amount of 95% alcoholic extract (fraction c) obtained from whole fruit of $Xylocarpus\ moluccensis$ optionally along with one or more pharmaceutically acceptable carriers, additives and diluents. The dosage of this composition may be administered at a unit dose of at least 250 to 500 mg/Kg body weight. The composition is preferably administered at a unit dose of 250 mg/Kg body weight wherein the sugar level is lowered up to 25.5% with the weight percentages representing percentages of the total weight of the sugar. The composition is preferably administered at a unit dose of 500 mg/Kg body weight wherein the total glycerides level is lowered up to 79% with the weight percentages representing percentages of the total weight of the total glycerides.

The composition comprises a therapeutically effective amount of chloroform fraction (fraction b) obtained from 50% alcoholic extract (fraction a) comprises Gedunin (14 to 19.8%), Photogedunin (1 to 1.5%) Carapolide-A (0.5 to 0.959%), Carapolide-B (0.01 to 0.279%), Xylocarpin (0.001 to 0.1%), Xyloccensin-H (0.01 to 1.7%), Xyloccensin-I (10 to 14.22%), Xyloccensin-U&F (3.5 to 6.7%), Palmitic acid (1.2 to 1.5%) β-Sitosterol-β-D-glucoside (0.9 to 1%) β-Sitosterol (2 to 2.1%), Oxogedunin (0.001 to 0.0001%), along with xyloccensin-T (3.5 to 5.8%) Xyloccensin-P 758 (4.0 to 7.067%), 674 xyloccensin-Q (10 to 13.65%), xyloccensin —R & xyloccensin-S (2 to 2.1%) and an unidentified unresolved fraction optionally along with one or more pharmaceutically acceptable carriers, additives and diluents. The dosage of this composition may be administered at a unit dose of at least 25 to 250 mg/Kg body weight. The composition is preferably administered at a unit dose of 100 mg/Kg body weight wherein the sugar level is lowered up to 22.3% with the weight percentages representing percentages of the total weight of the sugar. The composition is preferably administered at a unit dose of 125 mg/Kg body weight wherein the total glycerides level is lowered up to 63% with the weight percentages representing percentages of the total weight of the total glycerides.

The composition may comprise a therapeutically effective amount of 95% alcoholic extract (fraction c) obtained from whole fruit of Xylocarpus molluccensis optionally along with one or more pharmaceutically acceptable carriers, additives and diluents. The dosage of this composition may be administered at a unit dose of at least 250 to 500 mg/Kg body weight. The composition is preferably administered at a unit dose of 250 mg/Kg body weight wherein the sugar level is lowered up to 25.5% with the weight percentages representing percentages of the total weight of the sugar. The composition is preferably administered at a unit dose of 500 mg/Kg body weight wherein the total glycerides level is lowered up to 79% with the weight percentages representing percentages of the total weight of the total glycerides.

The composition may comprise a therapeutically effective amount of chloroform fraction (fraction d) obtained from 95% alcoholic extract (fraction c) comprises xyloccensin E (0.2-0.32%), xyloccensin 1 (0.22-0.32%), xyloccensin J (0.5-0.6%), xyloccensins X&Y (0.8-1%), phragmalin diacetate (5 to 8% of the chloroform fraction), palmitic acid (1 to 1.2% of the chloroform fraction), β-sitosterol (1.5 to 1.8% of the chloroform fraction) β-sitosterol-β-D-glucoside (0.1 to 0.15% of the chloroform fraction), protolimonoids (0.01 to 0.015% of the chloroform fraction), unidentified compounds (1.1-1.2%) and a unidentified unresolved fraction optionally along with one or more pharmaceutically acceptable carriers, additives and diluents. The dosage of this composition may be administered at a unit dose of at least 100 to 250 mg/Kg body weight. The composition is preferably administered at a unit dose of 100 mg/Kg body weight wherein the sugar level is lowered up to 10.1% with the weight percentages representing percentages of the total weight of the sugar. The composition is preferably administered at a unit dose of 250 mg/Kg body weight wherein the total glycerides level is lowered up to 89% with the weight percentages representing percentages of the total weight of the total glycerides.

The composition may comprise a therapeutically effective amount of chromatographic fraction (fraction e) obtained from the chloroform fraction (fraction d) comprising a mixture of limonoids optionally along with one or more pharmaceutically acceptable carriers, additives and diluents. The dosage of this composition may be administered at a unit dose of at least 25 to 100 mg/Kg body weight. The composition is preferably administered at a unit dose of 25 mg/Kg body weight wherein the sugar level is lowered up to 52.1% with the weight percentages representing percentages of the total weight of the sugar. The composition is preferably administered at a unit dose of 100 mg/Kg body weight wherein the total glycerides level is lowered up to 75% with the weight percentages representing percentages of the total weight of the total glycerides.

Further, the present invention provides a method of treating diabetes and dyslipidemia in a subject, wherein the method comprises the step of administering to the subject a pharmaceutical composition comprising a therapeutically effective amount of bioactive fractions optionally along with one or more pharmaceutically acceptable carriers, additives and diluents.

The method further includes the step of administering to the subject a pharmaceutical composition comprising a therapeutic effective amount of a 95% alcoholic extract (fraction c) obtained from whole fruit of *Xylocarpus moluccensis* optionally along with one or more pharmaceutically acceptable carriers, additives and diluents. This composition may be administered at a unit dose of at least 250 to 500 mg/Kg body weight. The composition is preferably administered at a unit dose of 250 mg/Kg body weight wherein the sugar level is lowered up to 25.5% with the weight percentages representing percentages of the total weight of the sugar. The composition is preferably administered at a unit dose of 500 mg/Kg body weight wherein the total glycerides level is lowered up to 79% with the weight percentages representing percentages of the total weight of the total glycerides.

The method includes the step of administering to the subject a pharmaceutical composition comprising a therapeutic effective amount of a chloroform fraction (fraction b) obtained from 50% alcoholic extract (fraction a) comprises Gedunin (14 to 19.8%), Photogedunin (1 to 1.5%) Carapolide-A (0.5 to 0.959%), Carapolide-B (0.01 to 0.279%), Xylocarpin (0.001 to 0.1%), Xyloccensin-H (0.01 to 1.7%), Xyloccensin-I (10 to 14.22%), Xyloccensin-U&F (3.5 to 6.7%), Palmitic acid (1.2 to 1.5%) β-Sitosterol-β-D-glucoside (0.9 to 1%), β-Sitosterol (2 to 2.1%), Oxogedunin (0.001 to 0.0001%), along with xyloccensin-T (3.5 to 5.8%) Xyloccensin-P 758 (4.0 to 7.067%), 674 xyloccensin-Q (10 to 13.65%), xyloccensin —R & xyloccensin-S (2 to 2.1%) and an unidentified unresolved fraction, optionally along with one or more pharmaceutically acceptable carriers, additives and diluents. This composition may be administered at a unit dose of at least 25 to 250 mg/Kg body weight. The composition is preferably administered at a unit dose of 100 mg/Kg body weight wherein the sugar level is lowered up to 22.3% with the weight percentages representing percentages of the total weight of the sugar. The composition is preferably administered at a unit dose of 125 mg/Kg body weight wherein the total glycerides level is lowered up to 63% with the weight percentages representing percentages of the total weight of the total glycerides.

The method further includes the step of administering to the subject a pharmaceutical composition comprising a therapeutic effective amount of a 95% alcoholic extract (fraction c) obtained from whole fruit of *Xylocarpus molluccensis* optionally along with one or more pharmaceutically acceptable carriers, additives and diluents. This composition may be administered at a unit dose of at least 250 to 500 mg/Kg body weight. The composition is preferably administered at a unit dose of 250 mg/Kg body weight wherein the sugar level is lowered up to 25.5% with the weight percentages representing percentages of the total weight of the sugar. The composition is preferably administered at a unit dose of 500 mg/Kg body weight wherein the total glycerides level is lowered up to 79% with the weight percentages representing percentages of the total weight of the total glycerides.

The method further includes the step of administering to the subject a pharmaceutical composition comprising a therapeutic effective amount of a xyloccensin E (0.2-0.32%), xyloccensin 1 (0.22-0.32%), xyloccensin J (0.5-0.6%), xyloccensins X & Y (0.8-1%) and phragmalin diacetate (5 to 8% of the chloroform fraction), palmitic acid (1 to 1.2% of the chloroform fraction), .beta.-sitosterol (1.5 to 1.8% of the chloroform fraction) .beta.-sitosterol-.beta.-D-glucoside (0.1 to 0.15% of the chloroform fraction), protolimonoids (0.01 to 0.015% of the chloroform fraction), unidentified compounds (1.1-1.2%) and an unidentified unresolved fraction, optionally along with one or more pharmaceutically acceptable carriers, additives and diluents. This composition may be administered at a unit dose of at least 100 to 250 mg/Kg body weight. The composition is preferably administered at a unit dose of 100 mg/Kg body weight wherein the sugar level is lowered up to 10.1% with the weight percentages representing percentages of the total weight of the sugar. The composition is preferably administered at a unit dose of 250 mg/Kg body weight wherein the total glycerides level is lowered up to 89% with the weight percentages representing percentages of the total weight of the total glycerides.

The method further includes the step of administering to the subject a pharmaceutical composition comprising a therapeutic effective amount of a chromatographic fraction (fraction e) obtained from the chloroform fraction (fraction d) comprises mixture of limonoids optionally along with one or more pharmaceutically acceptable carriers, additives and diluents. This composition may be administered at a unit dose of at least 25 to 100 mg/Kg body weight. The composition is preferably administered at a unit dose of 25 mg/Kg body weight wherein the sugar level is lowered up to 52.1% with the weight percentages representing percentages of the total weight of the sugar. The composition is preferably administered at a unit dose of 100 mg/Kg body weight wherein the total glycerides level is lowered up to 75% with the weight percentages representing percentages of the total weight of the total glycerides.

An oral administration route is preferably used for these methods.

The present invention also provides a process for the preparation of bioactive fractions from *Xylocarpus* selected from the group consisting of alcoholic fraction, chloroform fraction or chromatographic fraction, wherein the process comprises the steps of:

a) powdering the air dried plant parts of *Xylocarpus*, b) soaking the powdered plant parts obtained from step (a) in aqueous alcoholic solvent and removing the solvent by conventional methods to obtain alcoholic fraction;

c) macerating the alcoholic fraction obtained from step (b) with chloroform or subjecting the alcoholic fraction for extracting in solid-liquid extractor followed by partitioning it in a continuous liquid-liquid extractor using two immiscible solvents by downward displacement method to obtain the chloroform fraction; and d) chromatography of the chloroform fraction obtained from step (c) on RP-18 column to get the chromatographic fraction.

The plant species are preferably selected from the group consisting of *Xylocarpus granatum, Xylocarpus moluccensis*, and can be prepared from any plant part of the *Xylacarpus*.

The alcoholic fraction may be either 50% alcoholic fraction (fraction a) or 95% alcoholic fraction (fraction c). The alcoholic solvent used may be selected from the group consisting of ethanol, methanol or mixture thereof. The 50% alcoholic fraction (fraction a) comprises an ash content of about 20%-35%, an acid insoluble ash content of about 2%-3%, an ethylacetate extractive content of about 2%-5%, a n-butanol extractive content of about 5%-15%, a marker (Gedunin) content of about 1%-2.5% and an amount of an unidentified unresolved fraction.

The 50% alcoholic fraction (fraction a) may be obtained from epicarp of *Xylocarpus granatum*. The 95% alcoholic fraction (fraction c) may be obtained from whole fruit of *Xylocarpus moluccensis*. The chloroform fractions (fraction b and fraction d) may be obtained from either 50% alcoholic fraction (fraction a) or 95% alcoholic fraction (fraction c). The chloroform fraction (fraction b) may also be obtained from 50% alcoholic fraction. The chloroform fraction (fraction b) comprises Gedunin (14 to 19.8%), Photogedunin (1 to 1.5%) Carapolide-A (0.5 to 0.959%), Carapolide-B (0.01 to 0.279%), Xylocarpin (0.001 to 0.1%), Xyloccensin-H (0.01 to 1.7%), Xyloccensin-I (10 to 14.22%), Xyloccensin-U&F (3.5 to 6.7%), Palmitic acid (1.2 to 1.5%) .beta.-Sitosterol-.beta.-D-glucoside (0.9 to 1%), .beta.-Sitosterol (2 to 2.1%), Oxogedunin (0.001 to 0.0001%), along with xyloccensin-T (3.5 to 5.8%) Xyloccensin-P 758 (4.0 to 7.067%), 674 xyloccensin-Q (10 to 13.65%), xyloccensin —R & xyloccensin-S (2 to 2.1%) and an unidentified unresolved fraction. The chloroform fraction (fraction d) may be obtained from 95% alcoholic fraction (fraction c).

The chloroform fraction (fraction d) comprises xyloccensin E (0.2-0.32%), xyloccensin 1 (0.22-0.32%), xyloccensin J (0.5-0.6%), xyloccensins X&Y (0.8-1%), phragmalin diacetate (5 to 8% of the chloroform fraction), palmitic acid (1 to 1.2% of the chloroform fraction), β-sitosterol (1.5 to 1.8% of the chloroform fraction) β-sitosterol-β-D-glucoside (0.1 to 0.15% of the chloroform fraction), protolimonoids (0.01 to 0.015% of the chloroform fraction), unidentified compounds (1.1-1.2%) and a unidentified unresolved fraction.

The chromatographic fraction (fraction e) may be obtained from the chloroform fraction (fraction d). The chromatographic fraction (fraction e) generally comprises a mixture of limonoids.

Further, the present invention also provides the isomeric xyloccensins having the general structural formula

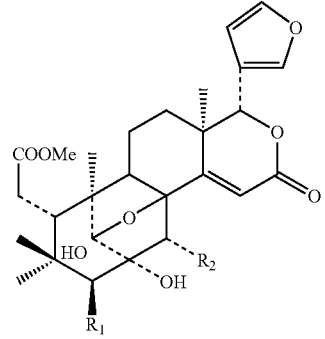

wherein

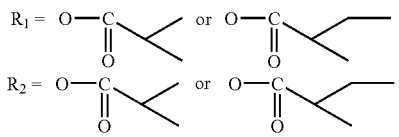

$R_1 \neq R_2$

The isomeric xyloccensins are the mixture of xyloccensin X having the structural formula

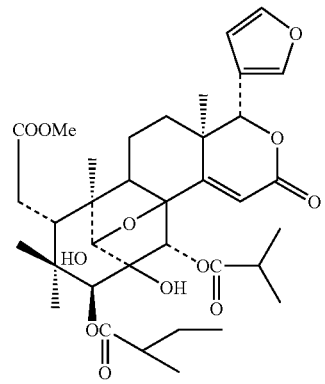

and xyloccensin Y having the structural formula

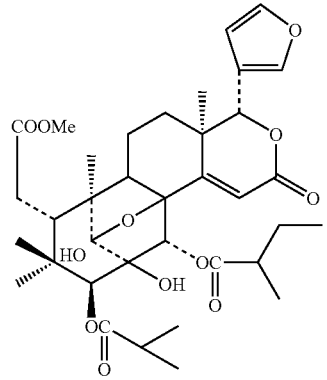

The xyloccensins are useful for the treatment of dyslipidemia. Further, thexyloccensins show optimum antidyslipidemic activity at a preferred unit dose of at least 50 mg/Kg body weight wherein the total glycerides level is lowered up to 19% with the weight percentages representing percentages of the total weight of the total glycerides. The xyloccensins show optimum antidyslipidemic activity at a preferred unit dose of at least 25 mg/Kg body weight wherein the free fatty acids level is lowered up to 47% with the weight percentages representing percentages of the total weight of the free fatty acids.

The present invention also provides the use of the isomeric xyloccensins in the treatment of dyslipidemia. Thexyloccensins show optimum antidyslipidemic activity at a preferred unit dose of at least 50 mg/Kg body weight wherein the total glycerides level is lowered up to 19% with the weight percentages representing percentages of the total weight of the total glycerides. Also, the xyloccensins show optimum antidyslipidemic activity at a preferred unit dose of at least 25 mg/Kg body weight wherein the free fatty acids level is lowered up to 47% with the weight percentages representing percentages of the total weight of the free fatty acids.

The present invention also provides a pharmaceutical composition useful as an antidyslipidemic agent comprising a therapeutically effective amount of isomeric xyloccensins optionally along with one or more pharmaceutically acceptable carriers, additives, lubricant and diluents. The diluents used may be selected from the group consisting of starch, lactose, and dicalcium phosphate. The lubricant used may be selected from the group consisting of talc, and magnesium stearate.

The dosage of this composition may be administered at a unit dose of at least 10 to 50 mg/Kg body weight. The composition is preferably administered at a unit dose of 50 mg/Kg body weight wherein the total glycerides level is lowered up to 19% with the weight percentages representing percentages of the total weight of the total glycerides. The composition preferably administered at a unit dose of 25 mg/Kg body weight wherein the free fatty acids level is lowered up to 47% with the weight percentages representing percentages of the total weight of the free fatty acids.

Further, the present invention provides a method of treating dyslipidemia in a subject, wherein the method comprises the step of administering to the subject a pharmaceutical composition comprising a therapeutically effective amount of isomeric xyloccensins optionally along with one or more pharmaceutically acceptable carriers, additives, lubricant and diluents. This composition may be administered at a unit dose of at least 10 to 50 mg/Kg body weight. The composition is preferably administered at a unit dose of at least 50 mg/Kg body weight wherein the total glycerides level is lowered up to 19% with the weight percentages representing percentages of the total weight of the total glycerides. Further, the composition is preferably administered at a unit dose of at least of 25 mg/Kg body weight wherein the free fatty acids level is lowered up to 47% with the weight percentages representing percentages of the total weight of the free fatty acids.

As noted the preferred administration route is orally.

The present invention relates to a process for the isolation of an antidiabetic and antidyslipidemic bioactive fraction from the fruits epicarp of the *Xylocarpus-granatum* and its use as an antidiabetic drug. The present invention has led to a new standardized antidiabetic and antidyslipidemic fraction having a high order of activity. The fraction has been standardized with the help of HPLC using standard chemical marker.

Fruits of the *Xylocarpus-granatum* mangrove were collected from South Andaman Coast in the month of January. Specimen sample (voucher specimen number 332, 373) has been preserved in the herbarium of the Botany Division at Central Drug Research Institute, Lucknow, India. These fruits were shade dried and three parts e.g. epicarp, seed coat, & seeds of the fruits were separated, as follows:

| (i)   | Epicarp   | (part A) |
| (ii)  | Seed coat | (part B) |
| (iii) | Seed      | (part C) |

Epicarp was used for the development of the antidiabetic and antidislipidemic fraction. Epicarp was about 25% of the total fruit.

The process for the isolation of standardized antidiabetic and antidislipidemic fraction from the fruit-epicarp of *Xylocarpus-granatum* involves the following steps
(1) Collection of the fruits from the Indian Coasts, shade drying, manual separation of the epicarp and its pounding.
(2) Powdered epicarp of the fruits were soaked in 50% aqueous-ethanol, number of times and was concentrated under reduced pressure below 50° C. to a dark brown powder (fraction a)
(3) It is a chocolate brown hygroscopic powder having an ash content of about 20%-35%, acid insoluble ash content of about 2%-3%, an ethylacetate extractive content of about 2%-5%, a n-butanol extractive content of about 5%-15% and a marker (Gedunin) content of about 1%-2.5% (in 50% aq. EtOH extract). Promising antidiabetic activity in rats has been shown in 50% Aqueous-ethanol extract as obtained in step-2.
(4) the dark-brown powder obtained in step-2 was macerated with hexane, chloroform & n-butanol successively to get respective fractions and the residual insoluble fraction.
(5) Bio-evaluation of these four fractions for antidiabetic and antidislipidemic activities in experimental animal models showed promising activities in (semi-polar solvents), chloroform extracted fraction.
(6) Major compounds present in chloroform fraction (fraction b) were identified by HPLC-MS of the product obtained in step-2 contained Gedunin (14 to 19.8%), Photogedunin (1 to 1.5%) Carapolide-A (0.5 to 0.959%), Carapolide-B (0.01 to 0.279%), Xylocarpin (0.001 to 0.1%), Xyloccensin-H (0.01 to 1.7%), Xyloccensin-I (10 to 14.22%), Xyloccensin-U&F (3.5 to 6.7%), Palmitic acid (1.2 to 1.5%) β-Sitosterol-β-D-glucoside (0.9 to 1%) β-Sitosterol (2 to 2.1%), Oxogedunin (0.001 to 0.0001%), along with xyloccensin-T (3.5 to 5.8%) Xyloccensin-P 758 (4.0 to 7.067%), 674 xyloccensin-Q (10 to 13.65%), xyloccensin-R & xyloccensin-S (2 to 2.1%) and an unidentified unresolved fraction.

Flow Chart 1

*Xylocarpus granatum* fruit's epicarp

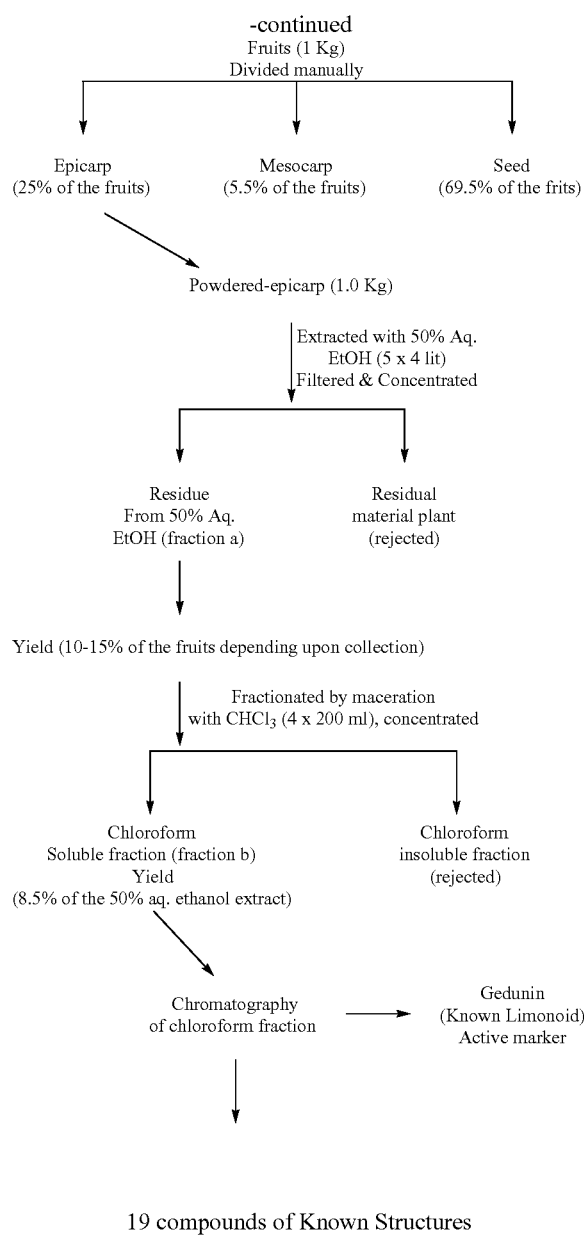

-continued
Fruits (1 Kg)
Divided manually

Epicarp (25% of the fruits) | Mesocarp (5.5% of the fruits) | Seed (69.5% of the frits)

Powdered-epicarp (1.0 Kg)

Extracted with 50% Aq. EtOH (5 x 4 lit) Filtered & Concentrated

Residue From 50% Aq. EtOH (fraction a) | Residual material plant (rejected)

Yield (10-15% of the fruits depending upon collection)

Fractionated by maceration with CHCl₃ (4 x 200 ml), concentrated

Chloroform Soluble fraction (fraction b) Yield (8.5% of the 50% aq. ethanol extract) | Chloroform insoluble fraction (rejected)

Chromatography of chloroform fraction → Gedunin (Known Limonoid) Active marker 19 compounds of Known Structures Standardized by HPLC-finger Printing (RP-18 Column) (Compounds Identified by LC-MS)

These have been used as markers for standardizing the fraction. Chloroform fraction was standardized by HPLC analysis using RP-18 column, eluting solvent water-acetonitrile (6:4 v/v) using UV-detector at wavelength 230, 254 and 275 nm.

(7) The marker, gedunin was found active in antidislipidemic hamster model and active in STZ-s and models.

TABLE 1

|  | Batch-I | Batch-II | Batch-III |
| --- | --- | --- | --- |
| 50% Aq. EtOH Extract. % Yield | 1999 collection B.S. No. 332 A 10% | 1999 collection B.S. No. 332 A 12% | 2001 collection B.S No. 373 A 15% |

Collections of fruits were made in 1999 & 2001. The ratio of seed coat, epicarp & seed in both the collection were as under

TABLE 2

|  | Batch I&II (1999 coll.) | Batch III (2001 coll.) |
| --- | --- | --- |
| Fruits | 100 kg | 100 kg |
| Epicarp | 25.0 kg (25%) | 27.0 kg (27%) |
| Seed coat | 5.5 kg (5.5%) | 5.1 kg (5.1%) |
| Seed | 69.5 kg (69.5%) | 67.9 kg (67.9%) |

The fruits of the *X. moluccensis* were collected from South Andaman Coast of India in the month of January, 1999, March, 2003, March, 2004 with voucher specimen numbers 338,424,433 respectively and from Orissa Coast in June 2002 with voucher specimen number 396. The sample specimen has been preserved in the Herbarium of the Botany Division, Central Drug Research Institute, Lucknow, India.

Fruits were shade dried after collection. Total fruits were used for the development of the antihyperglycemic and antidyslipidemic composition from the fruits of the *X. moluccensis*.

The preparation of composition involves the following steps:

1. Collection of the fruits from the Indian coasts, shade drying and its pounding.
2. Powdered fruits were soaked in 95% aqueous ethanol for 24 h. The resultant alcoholic extract was collected and concentrated under reduced pressure at 45°C. The process was repeated for 4 times to give a dark green viscous mass.
3. Ethanol extract (fraction c) as obtained in step-2 showed promising antihyperglycemic and antihyperlipidemic activities in the experimental animals.
4. The green viscous mass obtained in step-2 was macerated with hexane, chloroform and n-butanol successively to get the respective fractions and the residual insoluble fraction.
5. Bio-evaluation of these four fractions for antihyperlipidemic activity in dyslipidemic hamsters and antihyperglycemic activity in rats and db-db mice models showed promising activities in (semipolar organic solvents), chloroform fraction.
6. Major compounds present in chloroform fraction (fraction d) were isolated, purified, characterized and bio-assayed the product obtained in step-2 containing xyloccensins (5 to 8% of the chloroform fraction) palmitic acid (1 to 1.2% of the chloroform fraction) β-sitosterol (1.5 to 1.8% of the chloroform fraction) β-sitosterol-β-D-glucoside (0.1 to 0.15% of the chloroform fraction) protolimonoids (0.01 to 0.015% of the chloroform fraction) and few more unidentified compounds.
7. These have been used as markers for the standardization of the composition. Composition was standardized by HPLC analysis using RP-18 column, eluting solvent, water-acetonitrile (6:4, v/v) using UV-detector at the weave lengths 230,254,275 nm.
8. The markers xyloccensins, palmitic acid, β-sitosterol, β-sitosterol β-D-glucoside and chromatographic fraction (fraction e) which contain protolimonoids were tested in SLM, STZ-s models.

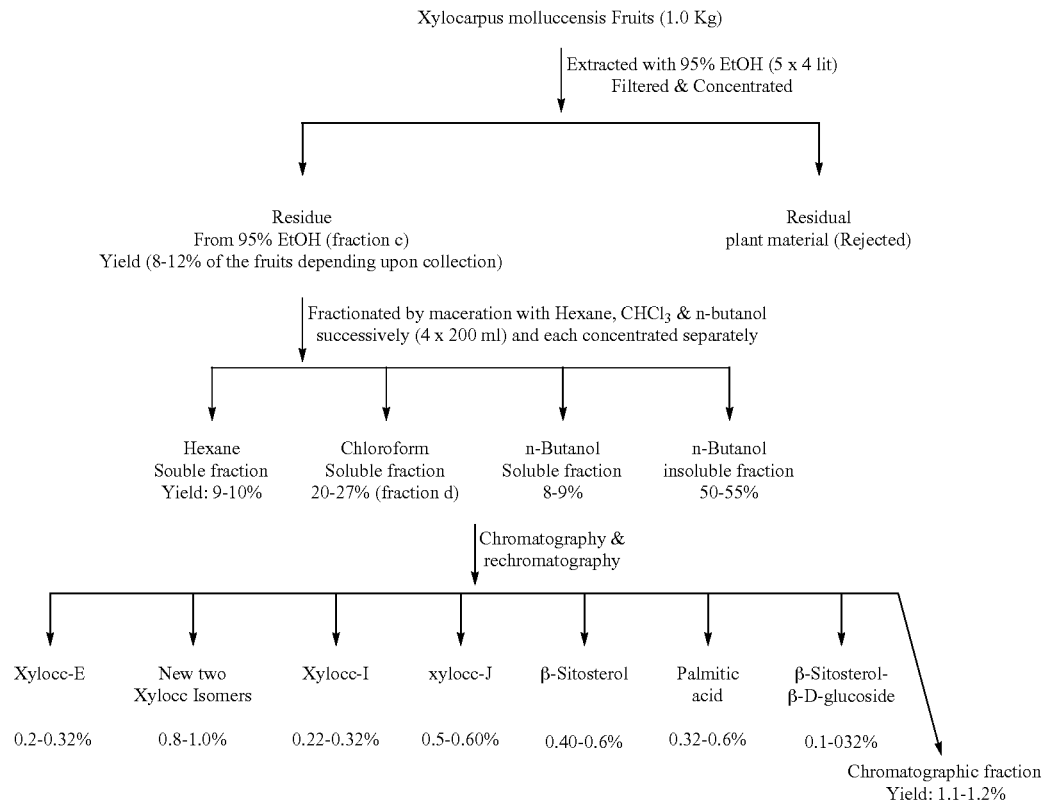

Flow Chart 2

TABLE 3

%Yield of the extract/fractions obtained from different collections

| S. No | Collection/extract/ fractions | Batch-I | Batch-II | Batch-III | Batch-IV |
|---|---|---|---|---|---|
| 1. | Collection place and Voucher | South Andaman of India (27 Jan. 1999) 338 | Orissa Coast of India (13 Jun. 2002) 396 | South Andaman of India (07 Mar. 2003) 424 | South Andaman of India (07 Mar. 2004) 433 |
| 2. | Ethanol extract | 8.49% of the fruits | 5.00% of the fruits | 8.01% of the fruits | 12.09% of the fruits |
| 3. | Hexane fraction of the ethanol extract | 9.66% of the | — | 3.43% of the ethanol extract | 2.51% of the ethanol extract |
| 4. | Chloroform fraction of the ethanol extract | 26.5% of the ethanol extract | — | 20.12% of the ethanol extract | 21.7% of the ethanol extract |
| 5. | n-Butanol fraction of the ethanol extract | 8.30% of the ethanol extract | — | 8.37% of the ethanol extract | — |
| 6. | n-Butanol insoluble part of the ethanol extract | 55.4% of the ethanol extract | — | 54.75% of the ethanol extract | 75% 0f the ethanol extract |

Identification by NMR:

The NMR spectra were recorded at 298K using a BRUKER Avance DRX 300 MHz Fourier transform NMR spectrometer equipped with a 5 mm multinuclear inverse probehead with z-shielded gradient. All experiments were done in CDCl$_3$ Chemical shifts are given on the δ scale and are referenced to TMS at 0.00 ppm for proton and 0.00 ppm for carbon.

In the ID measurement ($^1$H, $^{13}$C) 32K data points were used for the FID.

The $^1$H NMR spectrum revealed characteristic features of xyloccensin limonoids with substitution at C-2 position supported by the absence of any signal between 3.0-3.5 ppm. The detailed $^1$H and $^{13}$C assignments and 1 and 2 are presented in Table 4. The presence of two H-30 protons resonating at 5.58 and 5.61 ppm clearly suggested it to be a mixture of two compounds, as both of them did not showed any cross peak in the two-dimensional correlation spectrum (COSY). In similar manner the $^{13}$C NMR spectrum provided two distinct sets of signals for C-3 and C-30 methine carbons as well as for every carbon belonging to the side chin ester substitution, indicating the presence of two similar types of compounds in the mixture. These sets of resonances were separated in the range of 0.1-0.3 ppm only. Apart from these resonances all the other signals of the two compounds did not showed any disparity and the signals superimposes on each other as evident from the carbon and proton spectra.

Moreover, the $^{13}$C spectrum showed six carbonyl peaks out of which the one at 163.1 ppm corresponds to the lactone carbonyl (C-16) confirmed through the HMBC correlation. Another carbonyl at 173.7 ppm displayed long-range correlation with the methoxy proton at 3.69 ppm and with H-5 methine proton ($\delta_H$ 2.67, brd, 9.3 Hz) and was assigned as the C-7 carbonyl carbon. Apart from this, four other carbonyl signals at 175.0, 175.4, 176.9, and 177.1 ppm belong to the ester carbonyl functionality of the side chain. The HSQC correlation indicated presence of five methylene carbons three of which resonating at 14.9, 24.9, and 31.8 ppm were assigned as C-11, C-12 and C-6 carbon of the basic limonoid skeleton.

TABLE 4

$^1$H (HSQC) and $^{13}$C NMR data correlations of xyloccensin X (1) and xyloccensin Y (2) (300 and 75 MHz, CDCl$_3$).

| Carbon | $^1$H NMR $\delta_H$: mult; J(Hz) | | $^{13}$C NMR $\delta c$ | |
|---|---|---|---|---|
| No. | X (1) | Y (2) | X (1) | Y (2) |
| 1. | — | — | 108.8 | |
| 2. | — | — | 81.1 | |
| 3. | 4.82, s | 4.84, s | 82.6 | 825.5 |
| 4. | — | — | 38.6 | |
| 5. | 2.67, brd, 9.6 | | 40.1 | |
| 6a. | 2.41, m(o) | | 31.8 | |
| 6b. | 2.16, d(o), 10.2 | | — | |
| 7. | — | — | 173.7 | |
| 8. | — | — | 80.4 | |
| 9. | 2.20, t(o) | | 51.3 | |
| 10. | — | — | 42.2 | |
| 11α. | 1.81, m | | 14.9 | |
| 11β. | 2.37, brm(o) | | — | |
| 12α. | 1.40, m(o) | | 24.9 | |
| 12β. | 2.02, brm (o) | | — | |
| 13. | — | — | 38.8 | |
| 14. | — | — | 158.4 | |
| 15. | 6.17, s | | 118.5 | |
| 16. | — | — | 163.1 | |
| 17. | 4.91, brs | | 81.2 | |
| 18. | 1.21, s | | 19.5 | |
| 19. | 1.14, s | | 20.6 | |
| 20. | — | — | 119.9 | |
| 21. | 7.48, s | | 141.2 | |
| 22. | 6.41, s | | 109.9 | |
| 23. | 7.41, s | | 142.9 | |
| 28. | 0.79, brs | | 24.3 | |
| 29. | 1.31, s | | 21.5 | |
| 30. | 5.58, s (o) | 5.61, s (o) | 75.3 | 75.3 |
| 1'. | — | — | 175.4 | — |
| 2'. | 2.55, m (o) | | 34.2 | — |
| 3'. | 1.14, s (o) | | 18.7 | — |
| 4'. | 1.11, s (o) | | 18.5 | — |
| 5'. | — | — | 176.9 | — |
| 6'. | 2.34, m (o) | | 40.8 | — |
| 7'. | 1.39 and 1.63, m(o) | | 26.4 | — |
| 8'. | 0.92, t(o), 6.6 Hz | | 11.4 | — |
| 9'. | 1.19, s | | 16.1 | — |
| 1". | — | — | — | 177.1 |
| 2". | — | 2.50, m (o) | — | 34.0 |

TABLE 4-continued $^1$H (HSQC) and $^{13}$C NMR data correlations of xyloccensin X (1) and xyloccensin Y (2) (300 and 75 MHz, CDCl$_3$).

| Carbon | $^1$H NMR $\delta_H$: mult; J(Hz) | | $^{13}$C NMR $\delta c$ | |
|---|---|---|---|---|
| No. | X (1) | Y (2) | X (1) | Y (2) |
| 3". | — | 1.15, s (o) | — | 18.9 |
| 4". | — | 1.11, s (o) | — | 19.1 |
| 5". | — | — | — | 175.0 |
| 6". | — | 2.36, m (o) | — | 40.9 |
| 7". | — | 1.39 and 1.67 m (o) | — | 26.3 |
| 8". | — | 0.93, t (o), 7.5 Hz | — | 11.5 |
| 9". | — | 1.21, s(o) | — | 16.1 |
| 7-OMe. | 3.69, s | | 51.9 | |

EXAMPLES

The following examples are given by way of illustration of the present invention and should not be construed to limit the scope of present invention.

Example-1

Dry *Xylocarpus granatum* epicarp (25 g) was powdered and soaked in ethanol-water (1:1, r.t. 25-30° C., 4 times x50) overnight (18 hrs). All the extracts were decanted, mixed, filtered and concentrated under reduced pressure (20-50 mm/Hg). The light brown semi solid powdery mass was successively macerated with 4×50 ml each with chloroform, methanol (6.1 g, 24.4% yield). The chloroform insoluble concentrated methanol soluble extract was again macerated with 1-butanol to get 1-butanol soluble was 1.15 g, 4.6% yield, and insoluble (12.5 g, 50%) thus standardized chloroform fraction showed most of the in question activity and was obtained in an yield of (8.5%).

Example-2

X G Dry powdered epicarp (25 g) was extracted with ethanol-H$_2$O (1:1) as per example 1. The light brown powder was taken into solid liquid extractor (soxhlet) and was continuously extracted with for 18 hrs. The chloroform-methanol extract thus obtained (100 ml) was treated with activated charcoal (1 g) and filtered through filter paper. The light brown extract was concentrated under vacuum to dryness this extract was macerated with chloroform to obtain chloroform soluble fraction, which was concentrated to get brownish powder, yields (4.5%).

Example-3

The methanol, ethanol-water extract soluble extract was obtained as in example-2 and example 1. This extract dissolved in methanol (20 ml) and water (80 ml) and mixed with the immiscible solvent chloroform The chloroform was allowed to drop at the rate of 5 ml/min under vigorous stirring. After passing 250 ml of chloroform, the chloroform layer was separated. The chloroform layer thus obtained was again shaken with 50 ml of distilled water and the chloroform layer thus obtained was concentrated to dryness. The chloroform fraction thus prepared was obtained in a yield of (4.2%).

Example-4

Air dried fruits of *X. moluccensis* (25 g.) were powdered and soaked in 95% ethanol (50 ml.) and left it for over night (18 hrs.) at room temperature. The process was repeated for 4 times. All the extracts (4×5-ml) were combined and concentrated under reduced pressure (20-50 mm/Hg) to give a semi-solid mass (Yield, 8.49%). The light brown semi-solid powdery mass was successively macerated with 4×50 ml. each with hexane (9.66%), chloroform (26.5%), methanol (22.5%) and methanol insoluble portion (39.1%). The concentrated methanol chloroform insoluble extract was again macerated with 1-butanol to get 1-butanol soluble (28.3% yield of the methanol chloroform insoluble fraction of the ethanolic extract) and left over was insoluble fraction (70.1% yield of the methanol chloroform insoluble fraction of the ethanolic extract)). Thus standardized chloroform fraction showed most of the in question activities and was obtained in the yield of 26.5% of the ethanolic extract. The chloroform fraction thus obtained was chromatographed over column of silica gel (mesh 230-400) and finally by HPLC using reverse phase column $C_{18}$ silica based and eluent acetonitrile-water (6:4, v/v) at 230 and 254 nm in UV-detector. The xyloccensins and other compounds were obtained in the pure form.

Example-5

*X. moluccensis* dried powdered fruits (25 g.) were extracted with ethanol as per example-4. The green-viscous semi solid mass was taken into solid-liquid extractor (soxhlet) and was continuously extracted with methanol chloroform for 18 hours. The methanolic chloroform extract thus obtained (100 ml) was treated with active charcoal (1 g) and the filtered through filter paper. The light brown extract was concentrated under vacuum to dryness (Yield, 61.5% of the ethanol extract). This extract was macerated with chloroform to obtain chloroform soluble fraction from which was concentrated to get brownish powder (Yield 25.4% of the ethanol extract). This fraction was standardized as in example-1.

Example-6

The methanol soluble extract was obtained as in example-2-4. This extract was dissolved in methanol (20 ml.) and water (80 ml.) and mixed with immiscible solvent chloroform. The chloroform layer was allowed to drop at the rate of 5 ml/min. under vigorous stirring condition. After passing 250 ml. of chloroform, the chloroform layer was separated. The chloroform layer thus obtained was again shaken with 50 ml of distilled water and the chloroform layer thus obtained was concentrated to dryness. The chloroform fraction was obtained in a yield of 23.6% of the ethanol extract. The chloroform fraction obtained was standardized as in example-4.

Example 7

Test models Used for Evaluation of Antihyperglycemic Activity
[A] G L M—Models Procedure
Sparague-Dauley [SD] strain male albino rats of the body weight 160±20 g were selected for study. Animals in three cages were kept for 3-4 days under standard experimental conditions. Before the experiment animals were given standard pellet diet and fresh drinking water ad-libitum. Day '0'-Day before experiment, animals were kept on over night starvation by removing food pellets in the evening at 5.00 P.M. normal rats with blood glucose level between 60-80 mg/dl were selected for the experiments
Drug metformate was administered half an hour before glucose was given. Blood glucose level in both the control and drug treated rats was estimated, 30, 60 and 120 minutes. Post glucose administration, i.e. 30 minutes [drug administration]. 0 minutes [glucose administration] and then blood glucose level was estimated at 30, 60 and 120 minutes post glucose administration to know the antihyperglycemic activity. Statistical significance was done by AUC-method.
[B] (i) STZ-Model Procedure
Sprague-Dauley [SD] strain male albino rats of body weight 160±20 g were taken for study. Animals in 3 cage were kept for 7 days under standard experimental conditions before the experiment. Animals were given standard rat-pellet diet and tap-water ad-libitum. Day '0'-Day before experiment, animals were kept for overnight starvation. Day '1' STZ [Sigma Co. USA] was injected intraperitoneally to all the starved animals at a dose of 60 mg/kg, dissolved in 100 m M citrate buffer, pH 4.5. Day '2' rats remained as such in the same conditions. Food pellets were removed on the penultimate day at 5:00 P.M. in the evening and animals were kept on over night starvation. Day '3': Blood-glucose level was estimated between 9:30-10:00 A.M. in all the animals. Blood was taken from tail of the rats by stab-techniques and the glucose level was estimated using "Advantage Glucometer" of Boehringer Mannheim Co, USA. Animals with glucose level between 180-270 mg/dl were selected for antihyperglycemic screening on the same day. The rats were divided into two groups [minimum 5 animal in each group] with almost matched glucose level. Group-I was kept only for control [STZ-injection were given only]. Group II were treated with STZ+test samples. Following method was followed after this—
(i) At '0' minute in both control as well as drug treated groups followed by the observation at 60, 120, 180, 240, 300, 360, 420 minutes and 24 hours post treatment.
(ii) The presence of antidiabetic activity was calculated from the drug treated group with that of control each time interval starting from 60 minutes to 420 min. post glucose challenge.

$$\% \text{ Antihyperglycemic Activity} = \frac{\text{Average blood-sugar level of the test substance treated group test time} \times 100}{\text{Average blood-sugars level of control group at test time}}.$$

The extract/fraction/compounds found active were statistically analyzed to determine area under curve [AUC] by plotting the blood-glucose values against time.
[B] (ii) STZ-s Procedure
Male albino rats of Sprague Dawley strain of the body weight 160±20 g were selected for this study. Streptozotocin (Sigma, USA) was dissolved in 100 mM citrate buffer pH 4.5 and calculated amount of the fresh solution was injected to overnight fasted rats (45 mg./Kg.) intraperitoneally. Blood was checked 48 hours later by glucosetrips and animals showing blood glucose values between 144 to 270 mg./dl. (8 to 15 mM) were included in the experiments and termed diabetic. The diabetic animals were divided into groups comprising 5 to 6 animals in each group. Rats of experimental groups were administered suspension of the desired test samples orally (made in 1.0% gum acacia) at 250 mg/Kg body weight in the case of 50% aq. ethanol extract or the chloroform fraction and 100 mg/Kg. in case of the standard drug Metformin. The animals of the control group were given an equal amount of 1.0% gum acacia. A sucrose load of the 2.5 g/Kg of the body weight was given after 30 minutes of the drug administration. After 30 minutes of the post sucrose load blood glucose level was again checked by glucostrips at 30, 60, 90, 120, 180, 240, 300 minutes and 24 hours respectively. The animals not found diabetic after 24 hours post treatment of the test samples were not considered and omitted from the calculations and termed as non responders. The animals, which did not show any fall in blood glucose profile in a group while the others in that group, showed fall in blood glucose profile were also considered as non-responders. The food but not the water was withheld from the cages during the experimentation. Comparing the AUC of experimental and control groups determined the percent of antihyperglycemic activity. Statistical comparison between groups was made by the Student's "t" test.

Table-5a presents the antihyperglycemic activity profile of the 50% aq.ethanolic extract, its chloroform fraction and standard drug metformin respectively in sucrose challenged Streptozotocin induced diabetic rats.

[C] db/db Mice Procedure

The db/db mouse is a well-characterized model of type-2 diabetes. The background for the db/db mouse is the C57BL/Ks strain. The major deficiency of the C57BL.Ks Bom-db mouse (db/db) is lack of a functional leptin receptor. This leads to defective leptin signaling and a complete lack of feedback from leptin. Both the hypothalamic NPY content and secretion are consequently elevated, and this result in hyperphagia and decreased energy expenditure, obesity, insulin-resistance, hyperinsulinemia, hyperglycemia and dyslipidemia. The db/db mouse develops NIDDM from around week 10. The disease is stable until week 20, where destruction of pancreatic β-cells can be recognized clinically as decreasing levels of plasma insulin and very severe hypoglycemia. The db/db mouse has a maximal life span of 9-12 months. The advantage of using male mice for experimental purposes is that the fluctuations in plasma parameters are less than in females where the oestrogens cycle affects the clinical diabetes. The optimal age of db/db mice used for experiments will be from week-12 to 18 when they have developed NIDDM with diabetic dyslipidemia but still have functional β-cells in the pancreas. C57BL/KsBom-db mice 12-18 weeks, 40-50 g bred in the animal house of CDRI, Lucknow. 10 mice were housed in groups of (5 males and 5 females) were housed in groups of 5 individuals (same sex) in a room controlled for temperature (23±2.0° C.) and 12/12 hours light/dark cycle (light on 6.00AM.). Body weight was measured daily from day 1 to day 10. All animals had free access to fresh water and to normal chow except on the days of the post prandial protocol day 6 and during the overnight fast before the OGTT on day 10. The animals always had access to water during experimental periods. Blood glucose was checked every morning up till day 5. On day 6 post prandial protocol was employed, in this method blood glucose was checked at −0.5 h and 0 h. The test samples were given to the treatment group whereas vehicle received the only gum acacia (1.0%); the blood glucose was again checked at 1, 2, 3, 4 and 6 h posttest drug treatment. On day 8, blood was collected for serum insulin and lipid profile measurements and finally on day 10 an oral glucose tolerance test (OGTT) was performed after an overnight fasting. Blood glucose was measured at 0.0 min. post treatment, at this juncture glucose solution was given at a dose of 3 g./Kg. to all the groups including vehicle; the profile of blood glucose was checked at 30, 60, 90 and 120 minutes post glucose administration.

Table-5-a represents the antihyperglycemic activity profile of 50% Aq.-EtOH extract and chloroform soluble fraction of the aq.-ethanolic extract and the standard drug Roziglitazone in hyperglycemic and hyperinsulinemic db/db mice. The results of the antidiabetic evaluations of the epicarp extracts/fractions/compounds in GLM and STZ models are given in table-1

TABLE 5a

Antihyperglycemic activity of the extract/fractions/pure compounds

| No. | No. of extracts./Fractions/Compounds. | Dose mg/kg | GLM model in % lowering | In STZ model % lowering | Significance (AUC) |
|---|---|---|---|---|---|
| 1. | Aq. EtOH ext. (Batch-I) | 250 | | 22.3 | $P < 0.05$ |
| 2. | AQ. EtOH ext. (Batch-II) | 250 | | 18.10 | $P < 0.05$ |
| 3. | Aq. EtOH ext. (Batch-III-lot-1) | 250 | | 20.3 | $P < 0.05$ |
| 4. | Aq. EtOH ext. (Batch-III-lot-2) | 250 | | 12.6 | $P < 0.05$ |
| 5. | $CHCl_3$ soluble fraction of Aq. EtOH ext. | 100 | 6.43 | 22.3 | $P < 0.05$ |
| 6. | n-BuOH soluble fraction of Aq. EtOH ext. | 100 | 3.62 | Nil | |
| 7. | BuOH insoluble fraction of Aq. EtOH ext. | 100 | 1.54 | Nil | |
| 8. | Gedunin from $CHCl_3$ soluble fraction | 100 | | 10.5 | $P < 0.05$ |

Results and Discussion:

The aq. ethanolic extract of the three collections showed promising antihyperglycemic activity in STZ model at 250 mg/Kg dose level. The methanol soluble fraction of the aq. ethanolic extract was also found showing promising results on the same model at the same dose. On further fractionation of the aqueous ethanolic extract into chloroform soluble and other fractions (table-5a), the activity was localized only in chloroform soluble fraction at 100 mg/Kg dose level in STZ model. The major pure compound gedunin isolated from this fraction was also found showing promising activity in STZ model at 100 mg/Kg dose.

TABLE 5b

| S. No. | Name of the compounds | Dose mg/Kg | % Activity in STZ-s model |
|---|---|---|---|
| 1. | Photogedunin | 100 | +30.5 |
| 2. | Palmitic acid | 100 | −5.6 |
| 3. | β-Sitosterol-β-D-glucoside | 100 | +10.1 |

Results and Discussion:

The three compounds isolated from the active chloroform fraction when tested at 100 mg/Kg dose level in STZ-s model did not show any activity, except Gedunin given in table-1. The data of the table-5 b suggested that the compounds present in the chloroform fraction are showing synergistic effect.

TABLE 6

Antihyperglycemic activity of 50% Aq. EtOH extract, its chloroform fraction and standard drug Metformin in sucrose challenged low dosed Streptozotocin induced diabetic rats.

| Test samples | Dose (mg./Kg.) | % Antihyperglycemic activity | |
|---|---|---|---|
| | | 24 h | 5 h |
| 50% Aq. EtOH ext. | 250 | 28.7* | 29.18* |
| Chloroform fraction | 100 | 24.2** | 24.5** |
| Metformin | 100 | 26.5*** | 23.6*** |

*p < 0.05
**p < 0.01
***<p0.001(All these are statistical significance level which are internationally accepted data and is determined by "One way using various tests".)

TABLE 7

Antihyperglycemic activity of 50% aq. ethanol extract, its chloroform fraction and standard drug Metformin in Sucrose- challenged low dosed Streptozotocin-induced diabetic db/db-mice.

| Test samples | Dose (mg./Kg.) | % Antihyperglycemic activity | |
|---|---|---|---|
| | | Day 6 | Day 10 |
| 50% Aq. ethanolic extract (fraction a) | 250 | 8.72 | 23.9** |
| Chloroform fraction of the Aq. EtOH ext. (fraction b) | 250 | 4.97 | 12.2** |
| | 100 | 14.0 | 24.6** |
| Roziglitazone | 3.0 | 6.24* | 48.5*** |

*<p0.05
**<p0.01
***<p0.001(All these are statistical significance level which are internationally accepted data and is determined by "One way using various tests".)

Results and Discussion of Antihyperglycemic Activity:

The antihyperglycemic activity of 50% aq. ethanol extract was observed (12.6% to 22.3% at the dose of 250 mg/Kg dose level, Table-5a. Whereas in case of the chloroform fraction of the 50% aq.ethanol extract showed more promising results as compared to the 50% aq.ethanol extract (22.3% lowering at 100 mg/Kg dose level, Table-5a). Therefore it is obvious that the chloroform fraction is lowering the same percent of the sugar from blood plasma at a dose of 100 mg/Kg as compared to 250 mg/Kg of the aq. ethanol extract. $ED_{50}$ (Half of the animal responded at this dose) of the chloroform fraction is (fraction b) 67 mg/Kg body weight of the animals as compared to 243 mg/Kg of the 50% aq. ethanol extract (fraction a). Therefore the chloroform fraction (fraction b) is more than three times is more effective as compared to aq. ethanol extract (fraction a).

The antihyperglycemic activity of the chloroform fraction ranged from 14.0 to 24.6% at the dose of 100 mg/Kg dose level.

Example 8

Pharmaceutical Composition of *Xylocarpus granatum* (50% aq.EtOH Extract)

Each 15.0 g Sachet contains dicalcium phosphate, sodium benzoate, sodium carbomethoxy cellulose, Talcum powder and flavour as excipient and drug in 2.5 and 5% concentration for phase-I multiple dose clinical trial. The excipients composition for 225.0 g is as given below

| Dicalcium phosphate | 204.00 g |
|---|---|
| Sodium benzoate | 2.25 g |
| Sodium CMC | 6.00 g |
| Talcum powder | 12.00 g |
| Flavor powder | 0.75 g |
| Total= | 225 g |

Example 9

Test Models used for the Evaluation of the Antidyslipidemic Activity:

Male golden Syrian Hamsters weighing 120-130 g were divided into dyslipidemic and dislipidemic plus drug treated groups of the eight animals in each groups were used. Feeding with high fat diet (supplied by NOVO—NORDISK, Denmark, Cat produced Dyslipidemia. No-99122211). Dislipidemic hamsters had free access to HFD and water ad-libitum. throughout the experiment for ten days. The test sample was fed orally at a dose of 250 mg./kg. from day-4 to day-10 (7 days) in the HFD hamsters. Normal hamsters fed with HFD and given drug vehicle only, served as control animals. Body weight of each animal and diet intake of each animal group was recorded daily to check the effect of the drug on food intake and body weight of the animals. At the end of the experiment i.e. on day $10^{th}$, the blood of non fasted animals were withdrawn in two sets of tubes in which one set contains 120 µl NaF (4.5 mg./ml) and after 15 min. in cold, plasma was separated. Biochemical analysis of plasma with out NaF was performed on the same day for Triglycerides (TG) total Cholesterol (TC) HDL-Cholesterol using enzymatic diagnostic kits. Similarly the plasma containing NaF Glucose was assayed for glucose, glycerol and free Fatty acids (FFA) on Synchron CX-5. Clinical System Beckmann Coulter Instrument. The data was analysed for its significance on Prism Software (Table-8).

TABLE 8

Antidyslipidemic activity of the 50% aq.EtOH ext., its chloroform fraction and pure compound in dislipidemic hamster model

| Test Samples | Dose (mg/kg) | TG | CHOL | HDL | GLU | GLY | FFA | H/C |
|---|---|---|---|---|---|---|---|---|
| 50% Aq.EtOH extract (fraction a) | 500 | −60*** | −36*** | −37*** | +6 | −23 | +6 | NC |
| Chloroform fraction of | 25 | −38 | NC | +5 | +21 | −29* | −21 | NC |
| | 50 | −48* | NC | NC | +5 | −38** | −18 | NC |

TABLE 8-continued

Antidyslipidemic activity of the 50% aq.EtOH ext., its chloroform fraction and pure compound in dislipidemic hamster model

| Test Samples | Dose (mg/kg) | TG | CHOL | HDL | GLU | GLY | FFA | H/C |
|---|---|---|---|---|---|---|---|---|
| 50% Aq.EtOH extract | 125 | −63** | NC | +9 | NC | −37*** | −11 | NC |
|  | 250 | −52* | +15 | +17 | NC | −48*** | −15 | +4 |
| (fraction b) | 250 | −45* | +8 | +24 | +16 | −10 | −25 | +19 |
| Gedunin | 25 | −47*** | +14 | +27* | −28*** | −22 | −36*** | +11 |
| Fenofibrate (Standard Drug) | 108.24 (300 μ mole) | −42* | −18* | NC | −22 | −36** | −20* | +10 |

*<p0.05
**<p0.01
***<p0.001

Statistical analysis values, in which data were analyzed using Graph Pad Prism Ver. 3.02, one way analysis of variance 't' test (nonparametric test)

+] % Change in mean values, increase (+) decrease (−)
−]

TG - - - Triglycerides
CHOL - - - Cholesterol
HDL - - - High Density Lipoprotein
GLU - - - Glucose
GLY - - - Glycerol
FFA - - - Free Fatty Acid
H/C - - - High density lipoprotein/cholesterol ratio
NC - - - No change
HFD - - - High Fat Diet Results & Discussion:

Lowering in TG values (Table-8) of 50% aq.ethanol extract (fraction a) was found 60% as compared to high fat diet (HFD) fed control animals at the dose of 500 mg/Kg dose level. On the other hand its chloroform fraction (fraction b) shows similar lowering (63%) at the dose of 125 mg/Kg dose level. We have also observed no change in HDL/CHOL ratio in the case of 50% aq.ethanol extract, where as HDL/CHOL ratio also not changed increased by 78% at the dose of 125 mg/Kg. which is beneficial for cardio-vascular disease. Lowering of free fatty acids was also observed in case of chloroform fraction (fraction b), is also an additional advantage for health.

The ethanol extract of the *X. moluccensis* showed promising antidiabetic activity in SLM and STZ-s models at 250-mg/Kg dose level (table-9). On further fractionation, the activity was localized in chloroform fraction (table-9) at 100 mg/Kg dose which is more promising as compared to crude ethanol extract. On chromatography and rechromatography of the chloroform fraction, the pure isolated and compounds tested for antidiabetic activity (table-9) in STZ-s model at lower doses were found inactive, except the chromatographic column fraction of the chloroform fraction, which showed promising results at 25 mg/Kg dose in STZ-s model in two repeat experiments.

TABLE 9

The results of the antidiabetic evaluations of the extracts/fractions/compounds in SLM and STZ-$_s$ models. (Complete fruit)

| No. | No. of exts./frs./Compds. | Dose mg/kg | SLM model % lowering | STZ-$_s$ model 5 h | % change 24 h |
|---|---|---|---|---|---|
| 1 | EtOH extract (fraction c) | 250 | −17.4** | −19.8** | −25.5** |
| 2 | CHCl$_3$ soluble fraction of EtOH ext. (fraction d) | 100 | −26.3* | −20.0** | −10.1 |
|  |  | 100 | −23.7** | −20.9 | −14.2 |
| 3 | n-BuOH soluble fraction of EtOH ext. | 100 | — | — | — |
| 4 | Xyloccensin-E from CHCl$_3$ soluble fraction | 25 |  | −6.91 | −0.34 |
| 5 | Xyloccensin-I | 25 |  | Nil | Nil |
| 6 | β-Sitosterol | 25 |  | Nil | Nil |
| 7 | xyloccensin (X & Y) | 25 |  | +0.46 | +5.95 |
| 8 | Chromatographic fraction of the CHCl$_3$ (fraction e) | 25 | — | −15.4 | −13.8 |
|  |  | 25 | — | −51.4** | −52.1** |
| 9 | Metformin (Standard) | 25 |  | −23.6** | −26.5** |

*p < 0.05,
**p < 0.001.

TABLE 10

Antihyperglycemic activity chloroform fraction of the ethanol extract and Standard drug Roziglutazone in Sucrose-challenged low dosed Streptozotocin-induced diabetic db/db-mice.

| Test Samples | Dose (mg./Kg.) | Antihyperglycemic activity | | Anti-dislipidemic activity | | |
|---|---|---|---|---|---|---|
| | | Day 6 | Day 10 | TG | CHOL | HDL-C |
| Chloroform fraction of the EtOH ext.- (fraction d) | 100 | −4.08 | −14.3 ** | −32.3 | −4.03 | −11.9 |
| Chromatographic fraction of chloroform fraction (fraction e) | 100 | −9.30 | −30.6 ** | +8.09 | 30.4 | −+42.5 |
| Roziglitazone | 10 | −13.8 ** | −27.4 *** | −16.0 | −5.5 | +7.14 |

** <p0.01
*** p < 0.001

Results and Discussion:

The chloroform fraction and chromatographic fraction of the chloroform fraction when tested in db/db mice for antidiabetic effect, the chloroform fraction and chromatographic fraction both showed promising results at 100 mg/Kg dose (table-10). The chromatographic fraction was found more active as compared to chloroform fraction. The standard drug roziglutazone showed lowering at 10 mg/Kg dose level of the same order of activities.

TABLE 11A

Antidyslipidemic activity of the EtOH ext., its chloroform fraction and pure compound in dislipidemic hamster model

| | | | | | | | |
|---|---|---|---|---|---|---|---|
| n-Butanol soluble fraction of the EtOH extract | 250 | −49** | −12 | +29** | −48*** | +9 | +52 |
| | 250 | −39* | −20 | −9 | −20 | −20 | +28 |

| Test samples | Dose (mg/kg) | TG | CHOL | HDL | GLY | FFA | H/C |
|---|---|---|---|---|---|---|---|
| EtOH extract (fraction c) | 500 | −71** | −31* | +20** | −59*** | −39** | +57 |
| | 500 | −79*** | −17 | +50 | −68*** | −18 | +86 |
| | 500 | −58*** | −32** | −20 | −26 | −17 | +18 |
| | 500 | −60*** | −8 | +18 | −31*** | −30 | +29 |
| | 500 | −71*** | −2 | +53*** | −10 | −12 | +54 |
| Chloroform fraction of the ethanol extract. | 250 | −89*** | −33*** | +64 | −69*** | −33*** | +152 |
| | 250 | −52* | −22 | +70 | −40*** | −30 | +122 |
| | 100 | −55* | NC | +50 | −27 | −28* | +54 |
| n-Butanol insoluble fraction of the EtOH extract | 250 | −50** | +21* | +43*** | −37*** | +36*** | +19 |
| | 250 | −30 | −5 | −6 | −12 | −22 | NC |
| Fenofibrate (Standard drug) | 108.24 (300 μmole) | −42* | −18* | NC | −36** | −20* | +10 |

TABLE 11B

Antidyslipidemic activity of the column fraction and pure compounds of the chloroform fraction of the ethanol extract in dislipidemic hamster model

| Test samples | Dose (mg/kg) | TG | CHOL | HDL | GLY | FFA | H/C |
|---|---|---|---|---|---|---|---|
| Chromatographic fraction of | 10 | −13 | +8 | −5 | −3 | −26 | −12 |
| the chloroform fraction | 100 | −75** | −37 | +18 | −47*** | −60*** | +83 |
| Xyloccensin- E | 10 | −22 | −18 | −25 | NC | −43* | −10 |
| xyloccensins | 10 | −43 | −4 | NC | −3 | −28* | +3 |
| Mixture (X & Y) | 25 | −30* | NC | +6 | −16 | −47*** | +4 |
| | 50 | −45* | −20 | +21 | −19 | −44** | +50 |
| Xyloccensin- I | 25 | NC | NC | −5 | −5 | −17 | −7 |
| β- Sitosterol | 25 | −7 | NC | −5 | −14 | −38*** | −7 |
| Fenofibrate (Standard drug) | 108.24 (300 μmole) | −42* | −18* | NC | −36** | −20* | +10 |

Results and Discussion:

On chromatography of the chloroform fraction the pure compounds isolated and tested at lower doses (table-11B) did not show activity except new two xyloccensins mixture, it showed lowering of TG and FFA at different doses (table-11B)

ADVANTAGES OF THE INVENTION

The main advantages of the present invention are:
1. The present formulation is safe over the commercial available drugs for diabetes.
2. The process steps are simple and plant material used is easily available.

What is claimed is:

1. A diabetes or dyslipidemia treating composition comprising a bioactive fraction obtained from *Xylocarpus*, wherein the fraction is a 50% ethanolic fraction (fraction a), or a 95% ethanolic fraction (fraction c) wherein fraction c is obtained from whole shade dried fruit of *Xylocarpus moluccensis*, and fraction a is obtained from epicarp of *Xylocarpus granatum*, and wherein the bioactive fraction has antihyperglycemic or antidyslipidemic activity and is present in a dose amount which is effective after administration to a subject to reduce sugar level by 12.6 to 28.7% or to reduce glycerides by 60% to 79% by weight with the weight percentages representing percentages of the total weight of the total glycerides.

2. The bioactive fraction containing composition as claimed in claim 1, wherein fraction a comprises an ash content of about 20%-35%, an acid insoluble ash content of about 2%-3%, an ethylacetate extractive content of about 2%-5%, an n-butanol extractive content of about 5%-15%, a marker of Gedunin in an amount of about 1%-2.5% and an amount of an unidentified unresolved fraction.

3. A pharmaceutical composition comprising a therapeutically effective amount of the bioactive fraction containing composition as claimed in claim 1 optionally with one or more pharmaceutically acceptable carriers, additives, lubricant and diluents.

4. The pharmaceutical composition as claimed in claim 3, wherein one of a diluent is selected from the group consisting of starch, lactose, dicalcium phosphate and a lubricant selected from the group consisting of talc and magnesium stearate.

5. The composition of claim 1 wherein fraction a is present at a dose amount of 250 to 500 mg/kg body weight of the subject.

6. The composition of claim 5 wherein fraction a, when administered to a subject to lower the sugar level, is present in the composition at a unit dose of 250 mg/Kg body weight.

7. The composition of claim 5 wherein fraction a, when administered to a subject to lower glycerides, is present in the composition at a unit dose of 500 mg/Kg body weight.

8. A method of treating diabetes or dyslipidemia in a subject, which comprises administering to a subject in need of such treatment a therapeutically effective amount of the bioactive fraction containing composition as claimed in claim 1.

9. The method as claimed in claim 8, wherein fraction a comprises an ash content of about 20%-35%, an acid insoluble ash content of about 2%-3%, an ethylacetate extractive content of about 2%-5%, an n-butanol extractive content of about 5%-15%, a marker of Gedunin in an amount of about 1%-2.5% and an amount of an unidentified unresolved fraction and is administered at a dose effective to reduce sugar level by up to 28.7% or to reduce glycerides by up to 60% by weight.

10. A method of treating dyslipidemia in a subject, which comprises administering to a subject in need of such treatment a pharmaceutical composition as claimed in claim 3.

11. A method of treating dyslipidemia as claimed in claim 10, wherein the composition is administered at a unit dose of 250 to 500 mg/kg body weight.

12. A method of treating diabetes in a subject, which comprises administering to a subject in need of such treatment a pharmaceutical composition as claimed in claim 3.

13. A method of treating diabetes as claimed in claim 12, wherein the composition is administered at a unit dose of at least 10 to 50 mg/kg body weight.

* * * * *